(12) United States Patent
Saito et al.

(10) Patent No.: US 7,167,196 B2
(45) Date of Patent: *Jan. 23, 2007

(54) ENDOSCOPIC IMAGING SYSTEM MAKING IT POSSIBLE TO DETACHABLY ATTACH EXPANSION UNIT HAVING EXTERNAL EXPANSION FACILITY AND ADD EXPANSION FACILITY FOR IMPROVING CAPABILITY OF SYSTEM

(75) Inventors: Katsuyuki Saito, Tokyo (JP); Akihiko Mochida, Tokyo (JP); Noboru Kusamura, Tokyo (JP); Makoto Tsunakawa, Tokyo (JP); Hideki Tashiro, Tokyo (JP); Shinji Yamashita, Tokyo (JP); Kanichi Matsumoto, Tokyo (JP); Wataru Ohno, Tokyo (JP); Masahiro Hagihara, Tokyo (JP); Kazutaka Nakatsuchi, Tokyo (JP); Kuniaki Kami, Tokyo (JP); Kotaro Ogasawara, Tokyo (JP)

(73) Assignee: Olympus Corporation (JP)

( * ) Notice: Subject to any disclaimer, the term of this patent is extended or adjusted under 35 U.S.C. 154(b) by 589 days.

This patent is subject to a terminal disclaimer.

(21) Appl. No.: 10/046,830

(22) Filed: Jan. 17, 2002

(65) Prior Publication Data
US 2002/0196334 A1 Dec. 26, 2002

Related U.S. Application Data

(62) Division of application No. 09/120,559, filed on Jul. 22, 1998, now Pat. No. 6,538,687.

(30) Foreign Application Priority Data

| Jul. 23, 1997 | (JP) | H9-197114 |
| Jul. 28, 1997 | (JP) | H9-201565 |
| Jul. 31, 1997 | (JP) | H9-206679 |
| Aug. 1, 1997 | (JP) | H9-208123 |

(51) Int. Cl.
*H04N 7/18* (2006.01)
*A61B 1/00* (2006.01)

(52) U.S. Cl. .......... 348/65; 600/118
(58) Field of Classification Search .......... 348/65, 348/75, 72; 600/109, 117, 178, 118; 375/240.15
See application file for complete search history.

(56) References Cited

U.S. PATENT DOCUMENTS
(Continued)

FOREIGN PATENT DOCUMENTS
JP 7194527 8/1995

*Primary Examiner*—Gims Philippe
(74) *Attorney, Agent, or Firm*—Ostrolenk, Faber, Gerb & Soffen, LLP

(57) ABSTRACT

In an endoscopic imaging system, a signal representing an object image produced by a scope and projected by a camera head is processed by a CCU and displayed as an endoscopic image on a TV monitor. The object image is stored as digital image data on a memory in the CCU, read as image data of a still image, and recorded on a PC card mounted in a PC card slot. The PC card slot is formed in the front panel or the like of the CCU. A lid member or the like functioning as an anti-liquid invasion member and shield can be located at an opening of the slot.

10 Claims, 29 Drawing Sheets

U.S. PATENT DOCUMENTS

| | | | |
|---|---|---|---|
| 4,727,417 A | 2/1988 | Kanno et al. | 358/98 |
| 4,862,873 A | 9/1989 | Yajima et al. | 600/111 |
| 5,124,789 A | 6/1992 | Hiyama et al. | 358/98 |
| 5,379,757 A * | 1/1995 | Hiyama et al. | 600/109 |
| 5,510,840 A * | 4/1996 | Yonemitsu et al. | 375/240.15 |
| 5,526,493 A | 6/1996 | Shu | 710/101 |
| 5,592,216 A | 1/1997 | Uehara et al. | 348/74 |
| 5,697,885 A | 12/1997 | Konomura et al. | 600/109 |
| 5,740,801 A | 4/1998 | Branson | 128/653 |
| 5,872,756 A | 2/1999 | Shime | 369/77.1 |
| 5,967,969 A * | 10/1999 | Enomoto et al. | 600/117 |
| 5,980,450 A | 11/1999 | Thompson | 600/112 |
| 5,993,381 A | 11/1999 | Ito | 600/131 |
| 6,110,104 A | 8/2000 | Suzuki et al. | 600/124 |
| 6,184,922 B1 | 2/2001 | Saito et al. | 348/65 |
| 2002/0101507 A1* | 8/2002 | Saito et al. | 348/65 |
| 2003/0122927 A1* | 7/2003 | Saito et al. | 348/72 |

* cited by examiner

FACE

BACK

|  | LIGHT ADJUSTMENT | | TONE | CONTOUR ENHANCE-MENT |
|---|---|---|---|---|
|  | SPEED | LEVEL | | |
| URETEROSCOPE/ ARTHROSCOPE | LOW | LOW | BLUISH | HIGH |
| LAPAROSCOPE | HIGH | HIGH | REDDISH | LOW |

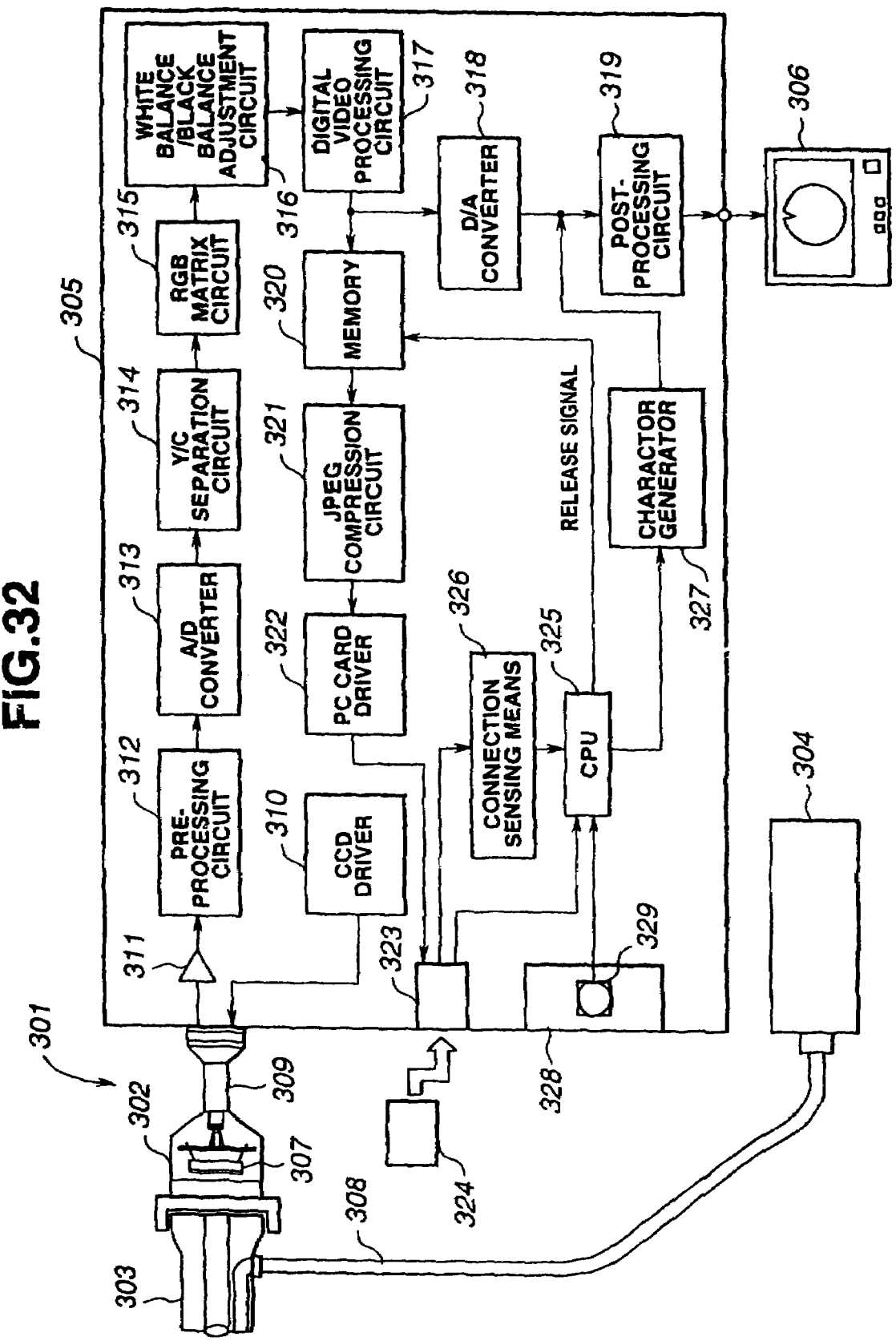

ENDOSCOPIC IMAGING SYSTEM MAKING IT POSSIBLE TO DETACHABLY ATTACH EXPANSION UNIT HAVING EXTERNAL EXPANSION FACILITY AND ADD EXPANSION FACILITY FOR IMPROVING CAPABILITY OF SYSTEM

This application is a divisional application of Ser. No. 09/120,559, filed Jul. 22, 1998, now U.S. Pat. No. 6,538,687, issued on Mar. 25, 2003. Priority is claimed under 35 U.S.C. §119 based on Japanese Application Nos. H9-197114, filed Jul. 23, 1997; H9-201565, filed Jul. 28, 1997; H9-206679, filed Jul. 31, 1997 and H9-208123, filed Aug. 1, 1997.

BACKGROUND OF THE INVENTION

1. Field of the Invention

The present invention relates to an endoscopic imaging system in which a view image produced by an endoscope is projected.

2. Description of the Related Art

Endoscopes having elongated insertion units thereof inserted into body cavities or the like and thus assisting in observation of object regions, various kinds of examinations, and cures and treatments have been widely adopted in the past. Assume that an optical endoscope such as a rigid scope or fiberscope is employed. In this case, generally, a camera head included in an endoscopic imaging system is attached to an eyepiece unit of the endoscope, and an endoscopic image is projected and viewed on a monitor or recorded for future diagnosis. Moreover, various types of endoscopic imaging systems including an electronic endoscope that is provided with an imaging device such as a CCD have been put to use.

An endoscopic image projected by an endoscopic imaging system may be recorded for use in a clinical record or thesis. In this case, generally, the image has been filmed as a photograph in the past. Alternatively, the image has been recorded as a motion picture on videotape by means of a VTR, or recorded as digital image data on an information-recording device such as a hard disk. Recently, a PC card having a memory incorporated as a card-shaped compact portable recording medium therein has become popular.

A conventional endoscopic imaging system has not been designed so that a freely-detachable compact portable recording medium such as a PC card or any other expansion unit that has an external expansion capability can be detachably attached to a main processor unit such as a camera control unit. If a medium can be mounted directly in the main processor unit, it would be quite convenient for reading image data on the PC card or the like and help expand the capability of the system readily. However, as far as the conventional system is concerned, an expansion slot in which the expansion unit is mounted must be included separately. This may lead to a complex system configuration and time-consuming handling and invite an increase in cost.

Moreover, a conventional endoscopic image to be recorded as a digital signal is compressed at a certain level of compressibility and then written on a recording medium according to the JPEG or the like. This poses a problem of poor use efficiency of the recording medium. Otherwise, an endoscopic imaging system permitting manual change of levels of compressibility is available. However, since a level of compressibility must be changed to another at every endoscopic examination, there arises a problem that handling becomes a nuisance. Another problem is that this feature is unacceptable at a medical site at which it is hard to touch the system.

Moreover, image quality such as a resolution requested for a medical image varies depending on an employed endoscope or solid-state imaging device, a medical field, or a lesion concerned. Image quality dealt with ranges from high quality permitting a high resolution to low quality suffering from a low resolution. If a certain level of compressibility is always used for compression, image data may be recorded at an unnecessarily low level of compressibility. This poses a problem that the use efficiency of a recording medium deteriorates.

Moreover, the situation of an object to be represented by an endoscopic image varies depending on a field in which the endoscopic imaging system is employed. For example, when a large-diameter laparoscope is employed, a picture size corresponds to a full size of a monitor screen. The tone of an object image is reddish as a whole. In the field of urology, a small-diameter rigid scope is employed. The picture size corresponds to the size of part of the monitor screen. The tone of an object image is whitish.

For coping with the various use situations, a technology has been disclosed in, for example, Japanese Unexamined Patent Publication No. 7-194527. Herein, a ROM in which setting data is stored is incorporated in an endoscope. A control unit reads the setting data, and modifies a sequence of controlling light adjustment or the like. However, a rigid scope employed in a surgical procedure and a camera head included in an endoscopic imaging system may be used in combination. A plurality of types of endoscopes may be attached to the camera head. There is difficulty in storing the setting data in the endoscopes. Even when the camera head is provided with a ROM for storing the setting data, it is rather meaningless.

As mentioned above, a ROM in which setting data is stored is incorporated in an endoscope, and a control unit references the setting data to modify a setting for an operation such as light adjustment. Thus, the conventional system is adjusted to specifications for endoscopes that are different from field to field, situations of objects, and other different use situations. However, an endoscope system may be constructed by combining an optical endoscope such as a rigid scope and a camera head included in an endoscopic imaging system. In this case, there are problems in that it is hard to store setting data in the endoscope, and a setting for an operation such as light adjustment cannot be modified according to a use situation.

Moreover, when the conventional endoscopic imaging system is employed, a produced endoscopic image may be recorded on a compact portable recording medium which is freely attachable and detachable, such as a PC card. In this case, the recorded situation of image data on the medium is unclear to a user. This may result in such a drawback that necessary image data cannot be recorded or stored reliably. That is, an image cannot be recorded because of insufficient capacity, or previously recorded image data is overwritten. Moreover, if the PC card is improperly inserted or connected, recording of an image may fail.

SUMMARY OF THE INVENTION

An aspect of the present invention is to provide an endoscopic imaging system making it possible to detachably attach an expansion unit which has an external expansion to a main unit, and to readily add an expansion facility for improving the capability of the system.

Another aspect of the present invention is to provide an endoscopic imaging system making it possible to automatically compress an endoscopic image at an optimal level of compressibility, and to thus improve the use efficiency of a recording medium.

Still another aspect of the present invention is to provide an endoscopic imaging system making it possible to readily achieve a proper setting for an operation according to a use situation.

Yet another aspect of the present invention is to provide an endoscopic imaging system making it possible to readily check the recorded situation of image data on a medium, and to thus prevent occurrence of an error during image recording.

In an endoscopic imaging system according to the present invention, a main processor unit including a signal processing means for processing a video signal representing an object image projected by an imaging means is provided with an expansion slot to which an expansion unit having an external expansion capability is freely detachably connected. When an expansion unit having an external expansion capability is detachably attached to the main unit, the expansion facility can be added to the system readily. Thus, the capability of the system can be improved.

Other features and advantages of the present invention will be fully apparent from the description below.

BRIEF DESCRIPTION OF THE DRAWINGS

FIG. 1 is a block diagram showing an overall configuration of an endoscopic imaging system;

FIG. 3 is a diagram showing a variant of the camera control unit, which is shown in FIG. 1, included in the endoscopic imaging system whose capability can be expanded;

FIG. 4 is a front view showing a structure of an expansion slot;

FIG. 5 is a sectional view of the expansion slot shown in FIG. 4;

FIG. 6 is a sectional view showing a structure of an expansion slot;

FIG. 7 is a sectional view showing a structure of a variant of the expansion slot shown in FIG. 6;

FIG. 8 is a sectional view showing a structure of an expansion slot;

FIG. 9 is a sectional view showing a structure of an outer side of the expansion slot shown in FIG. 8 and its surroundings with an expansion unit mounted in the expansion slot;

FIG. 10 is an oblique view showing component members to be assembled into the expansion slot shown in FIG. 8;

FIG. 11 is an oblique view showing a structure of the expansion unit shown in FIG. 9 which is seen from the face thereof;

FIG. 12 is an oblique view showing the structure of the expansion unit shown in FIG. 9 which is seen from the back thereof;

FIG. 13 is an oblique view showing a structure of a variant of the expansion unit shown in FIG. 11;

FIG. 14 is a sectional view showing a structure of a first variant of the expansion slot shown in FIG. 8;

FIG. 15 is a diagram showing a structure of a second variant of the expansion slot shown in FIG. 8;

FIG. 16 is a diagram showing a structure of a third variant of the expansion slot shown in FIG. 8;

FIG. 17 is a diagram showing a configuration of an endoscopic imaging system;

FIG. 18 is a diagram showing a configuration of an expansion unit shown in FIG. 17;

FIG. 19 is a flowchart describing the operation of the endoscopic imaging system shown in FIG. 17;

FIG. 20 is a diagram showing a configuration of a variant of the endoscopic imaging system shown in FIG. 17;

FIG. 21 is an oblique view showing the overall appearance of an endoscopic imaging system;

FIG. 22 is an explanatory diagram showing a system configuration permitting connection of a plurality of types of endoscopes;

FIG. 23 is a block diagram showing a functional configuration of an endoscopic imaging system;

FIG. 24 is a front view showing a layout of components on the front panel of a camera control unit;

FIG. 25 is an explanatory diagram showing a situation in which an object image produced by a small-diameter scope is displayed;

FIG. 26 is an explanatory diagram showing a situation in which an object image produced by a large-diameter scope is displayed;

FIG. 27 is an explanatory diagram showing an example of setting data representing adjustment values associated with various fields;

FIG. 28 is a flowchart describing an alarm operation to be carried out when an incorrect memory card is inserted;

FIG. 29 is an explanatory diagram showing an example of an alarm display;

FIG. 30 is an explanatory diagram showing a memory card dedicated to Dr. A out of a plurality of kinds of memory cards associated with doctors;

FIG. 31 is an explanatory diagram showing a memory card dedicated to Dr. B out of the plurality of kinds of memory cards associated with doctors;

FIGS. 32 to 36 relate to an eighth embodiment of the present invention;

FIG. 32 is a block diagram showing an overall configuration of an endoscopic imaging system;

FIG. 33 is a front view showing a layout of components on the front panel of a camera control unit;

FIG. 34 is a block diagram showing a configuration of an image recording unit;

FIG. 35 is a block diagram showing a functional configuration of a JPEG compression circuit;

FIG. 36 is an explanatory diagram showing a screen display on a monitor;

FIG. 37 is a block diagram showing an overall configuration of an endoscopic imaging system;

FIG. 38 is an explanatory diagram showing an information display on a liquid crystal display placed on the front panel of the camera control unit;

FIG. 39 is a block diagram showing an overall configuration of an endoscopic imaging system;

FIG. 40 is an explanatory diagram showing a screen display on a monitor;

FIG. 41 is a block diagram showing an overall configuration of an endoscopic imaging system;

FIG. 42 is an explanatory diagram showing a screen display on a monitor;

FIG. 43 is a block diagram showing an overall configuration of an endoscopic imaging system;

FIG. 44 is a front view showing a layout-of components on the front panel of a camera control unit;

DESCRIPTION OF THE PREFERRED EMBODIMENTS

First Embodiment

Figure 1:
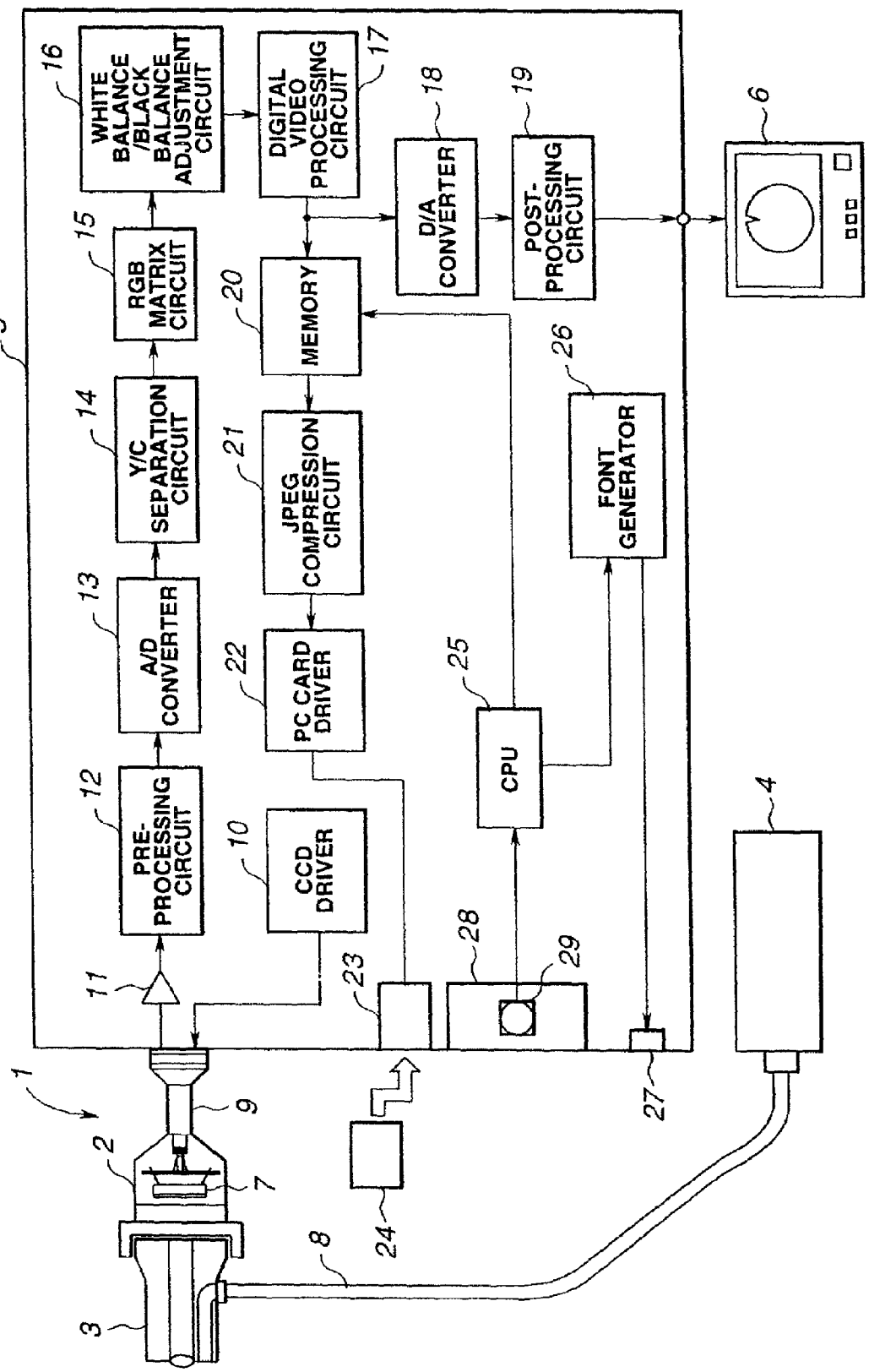
FIGS. 1 and 3 relate to a first embodiment of the present invention.

As shown in FIG. 1, an endoscopic imaging system 1 of this embodiment comprises a camera head 2 having an imaging means incorporated therein, a scope 3 connected to the camera head 2, a light source apparatus 4 for supplying illumination light to the scope 3, a camera control unit 5 (hereinafter a CCU) serving as a main processor unit for processing a signal sent from the imaging means incorporated in the camera head 2, and a TV monitor 6 for displaying a standard video signal processed by the CCU 5. The scope 3 is a rigid endoscope such as a laparoscope used for, for example, a surgical procedure in the field of surgery.

When the endoscope imaging system 1 is in use, a light guide 8 of the scope 3 is, as shown in FIG. 1, linked to the light source apparatus 4. Illumination light emanating from a lamp in the light source apparatus 4 passes through a diaphragm that is not shown, is converged by a lens, and falls on the opposing end surface of the light guide 8. The illumination light is transmitted to the scope 3 over the light guide 8, passes through the scope 3, and is emitted forward through the distal end of the scope 3. Thus, an object in a patient's body cavity or the like is illuminated. An image represented by light reflected from the illuminated object is formed by the scope 3. A resultant object image is projected by the imaging means in the camera head 2 through the scope 3.

A CCD 7 serving as the imaging means is located on the focal plane of an imaging lens in the camera head 2. The object image is formed on the image plane of the CCD 7, and photoelectronically converted. The CCD 7 is connected to the CCU 5 by a camera cable 9 having a CCD driving signal transmission line and CCD output signal transmission line inserted therein. An output signal of the CCD 7 is sent to the CCU 5, and subjected to various kinds of signal processing.

A video signal output from the CCU 5 is sent to the TV monitor 6. A view image of the object is then displayed on the TV monitor 6.

The CCU 5 is provided with a CCD driver 10. The CCD driver 10 supplies a CCD driving signal to the CCD 7 over the CCD driving signal transmission line in the camera cable 9, and reads a signal charge accumulated in the CCD 7. Moreover, the CCU 5 is provided with a preamplifier 11 and pre-processing circuit 12. A CCD output signal read by the CCD 7 is transmitted to the CCU 5 over the CCD output signal transmission line in the camera cable 9. After the CCD output signal is amplified by the preamplifier 11 in the CCU 5 in order to compensate for a loss occurring on the cable, it is input to the pre-pocessing circuit 12.

On the succeeding side of the pre-processing circuit 12, there are an A/D converter 13 and Y/C separation circuit 14. The CCD output signal input to the pre-processing circuit 12 is pre-processed by carrying out correlation double sampling (CDS) and sample-and-hold (S/H). The resultant CCD output signal is input to the A/D converter 13 and converted into a digital signal, and then input to the Y/C separation circuit 14.

On the succeeding side of the Y/C separation circuit 14, there are an RGB matrix circuit 15 and a white balance/black balance adjustment circuit 16. The digital signal input to the Y/C separation circuit 14 is recomposed according to the line-sequential system. Three digital signals Y, CR, and CB propagating through different channels and constituting the digital signal are then separated from one another, input to the RGB matrix circuit 15, and converted into an RGB digital signal. Thereafter, the white balance/black balance adjustment circuit 16 adjusts the white balance and black balance of the RGB digital signal.

On the succeeding side of the white balance/black balance adjustment circuit 16, there are a digital video processing circuit 17, a D/A converter 18, and a post-processing circuit 19. The RGB digital signal having undergone balance adjustment is digitally processed through enhancement, gamma correction, and character convolution carried out by the digital video processing circuit 17. Thereafter, the resultant signal is converted into an analog signal by the D/A converter 18, and then input to the post-processing circuit 19. The analog signal that is input to the post-processing circuit 19 is converted into a standard video signal, and then output to the TV monitor 6.

Moreover, on the succeeding side of the digital video processing circuit 17, there are a memory 20, a JPEG compression circuit 21, and a PC card driver 22. A PC card slot 23 is connected to the PC card driver 22. The digital signal having undergone various kinds of signal processing is stored in the memory 20. A PC card 24 having a memory incorporated therein is mounted in the PC card slot 23. A digital image signal read from the memory 20 is compressed by the JPEG compression circuit 21, and then recorded on the PC card 24 via the PC card driver 22.

Furthermore, the CCU 5 is provided with a CPU 25 responsible for various kinds of control including control of image recording on the PC card 24, and a font generator 26 for outputting a display of medium information including the number of image data items recordable on the PC card 24. Located on the front panel 28 of the CCU 5 are a release switch 29 used to provide a handling instruction (release instruction) for image recording and an LED 27 for displaying the medium information.

Figure 2:
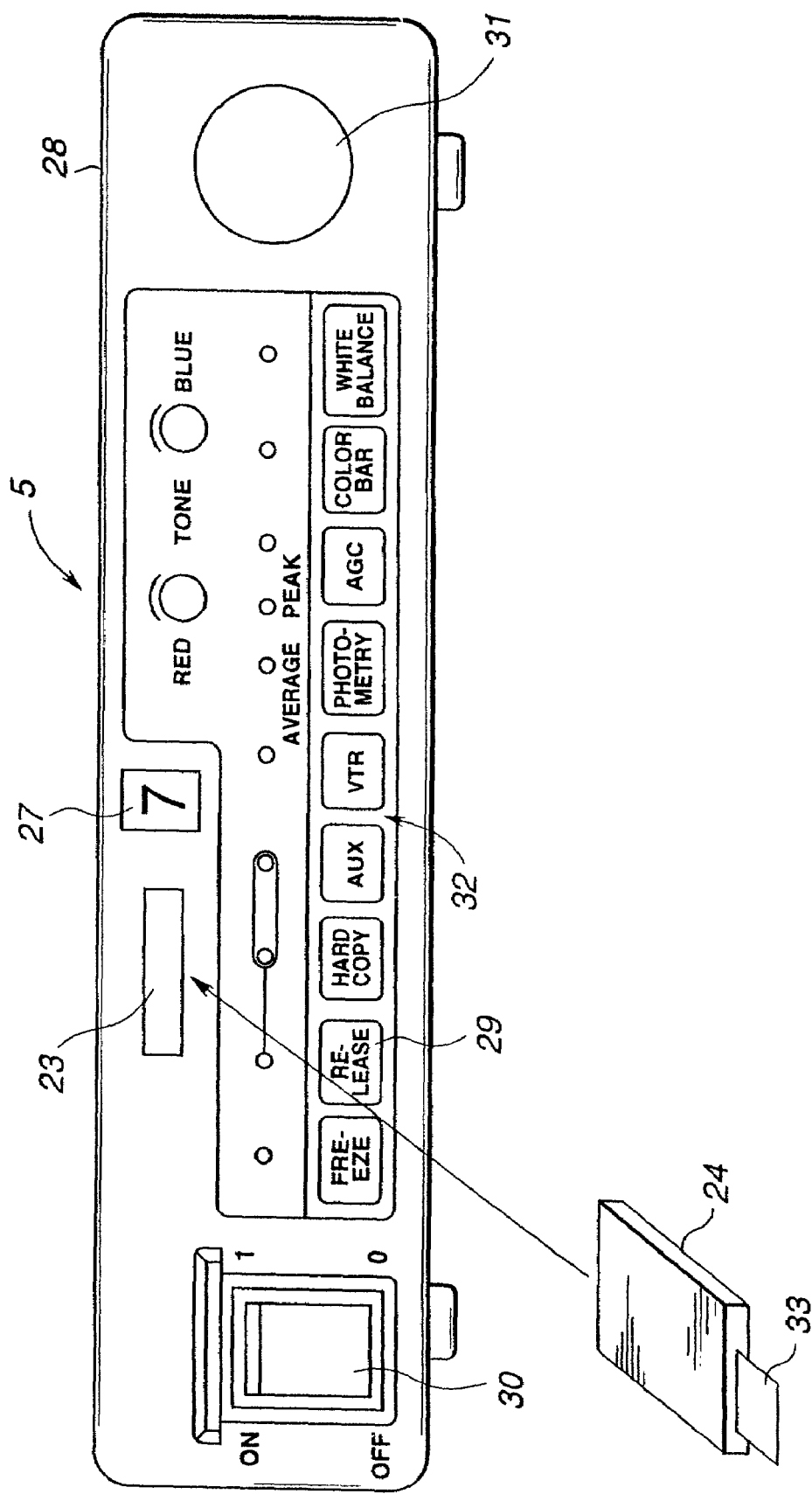
FIG. 2 is a front view showing a configuration of a front panel of a camera control unit shown in FIG. 1.

As shown in FIG. 2, a power switch 30, a connector receptor 31 into which the camera head 2 is plugged, the PC card slot 23, the LED 27, and operation switches 32 including the release switch 29 are arranged on the front panel 28 of the CCU 5. A compact memory card 33 such as a smart medium is detachably attached to the PC card 24.

In the endoscopic imaging system 1 having the foregoing components, an image signal produced by the scope 3 and visualized and processed by the camera head 2 is output to the TV monitor 6 and displayed in the form of an image. Additionally, the image signal is stored in the memory 20.

When the release switch 29 is pressed for recording an endoscopic image, the CPU 25 sends a release signal to the memory 20. Image data representing a still image is read from the memory 20. The read image data is compressed by the JPEG compression circuit 21. The image data is then sent to the PC card 24 mounted in the PC card slot 23 via the PC card driver 22, and then recorded.

Moreover, for image recording, medium information including the quantity of released image data representing a still image, i.e., the number of image data items recorded on the PC card 24 is sent from the CPU 25 to the font generator 26. The font generator 26 outputs the information as character information. The character information is then displayed in the LED 27 for displaying medium information on the front panel. The quantity is indicated with numerals in the LED 27 and is incremented by one with every release.

When an endoscopic image is thus recorded using the PC card, recording and storage of a still image with little quality deterioration can be easily realized and at low cost. Thus, medium information including the number of image data items recorded on the PC card is displayed in the LED on the front panel of the CCU. This allows a user to readily check the number of remaining recordable images.

Moreover, the PC card slot may be formed in the front panel of the CCU so that the PC card can be detachably attached directly. This makes it possible to expand the capability of the system with ease and good handling efficiency. Consequently, the capability of the system can be improved.

Figure 3:
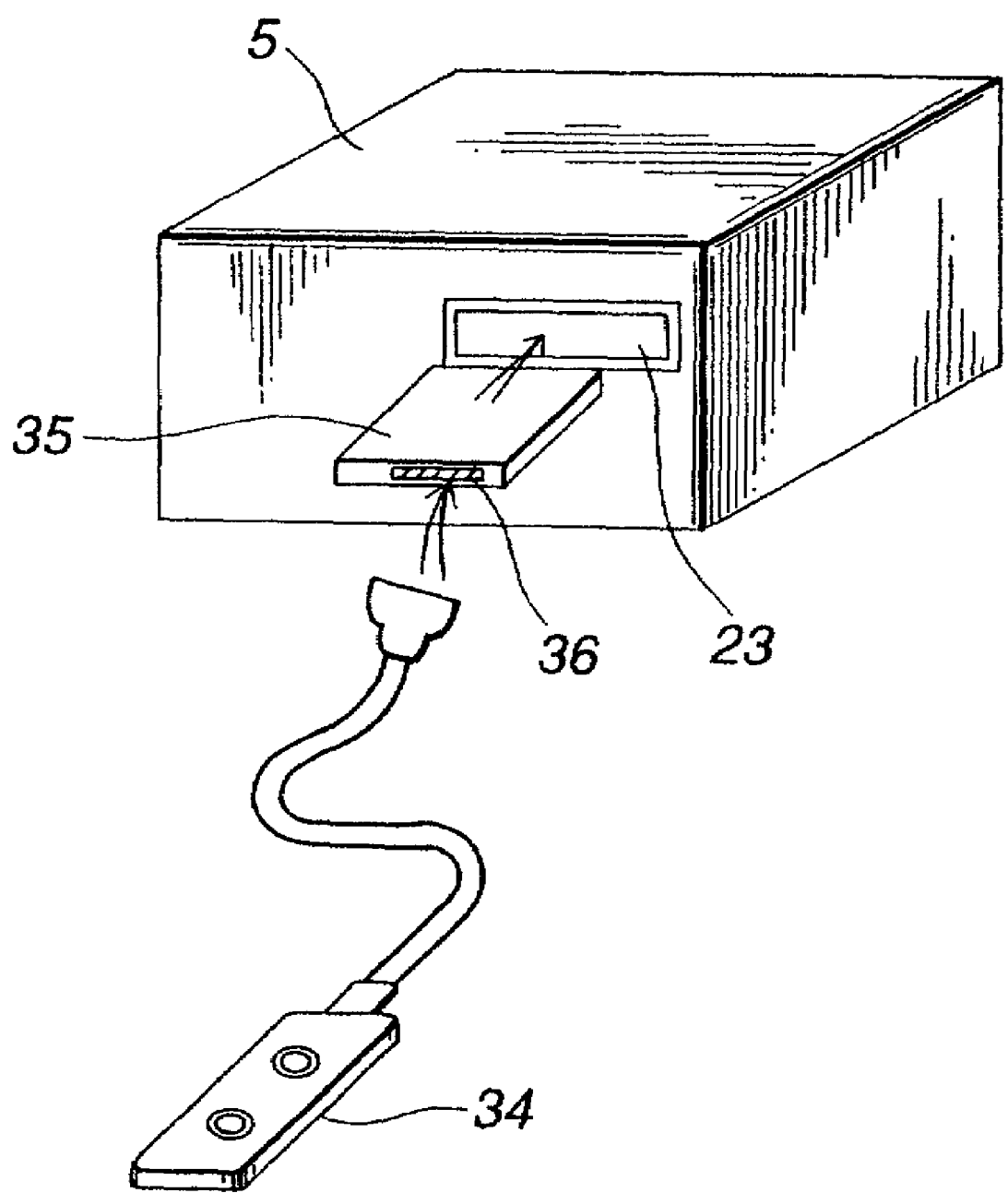

FIG. 3 shows a variant of an endoscopic imaging system whose capability can be expanded. In the CCU 5 of this variant, a PC card 35 to which a remote control unit 34 can be connected is detachably attached to the PC card slot 23 in the front panel. The remote control unit 34 has a CPU which controls remote control-related facilities on a centralized basis and is independent of the CPU in the CCU 5, incorporated therein. When the remote control unit 34 is plugged into a remote control terminal 36 of the PC card 35, the CCU 5 or the like can be handled and controlled using the remote control unit 34.

In other words, the remote control unit is connected to the PC card slot 23 via the PC card for recording image data as described in conjunction with the previous embodiment. Thus, control signals or the like can be transferred via a digital input/output interface in the slot.

According to this configuration, a remote control facility desired by a user can be controlled without use of the CPU in the CCU. This obviates the necessity of including an interface dedicated to remote control in the CCU. Consequently, the configuration of the system can be simplified and the cost thereof can be minimized.

An expansion unit to which the remote control unit is connected is not limited to a PC card. The remote control unit may be connected to any other expansion unit that can be detachably attached to the CCU. Otherwise, a CPU or the like may be incorporated in an expansion unit itself so that the remote control facilities can be installed in the CPU.

In this embodiment, an expansion slot in which an expansion unit is mounted is formed in a main processor unit included in an endoscopic imaging system. The expansion unit intended for external expansion capability, for example, a compact portable recording medium which is freely detachable and attachable, such as a PC card, can be detachably attached to the expansion slot. In this case, liquid may be spilled over the main processor unit because of user's carelessness during an examination or surgical procedure. The liquid may then invade into the expansion slot. This would bring about a short circuit between electrical contacts or corrosion in the main processor unit. A structure for preventing invasion of liquid is therefore needed.

Second Embodiment

Figure 45:
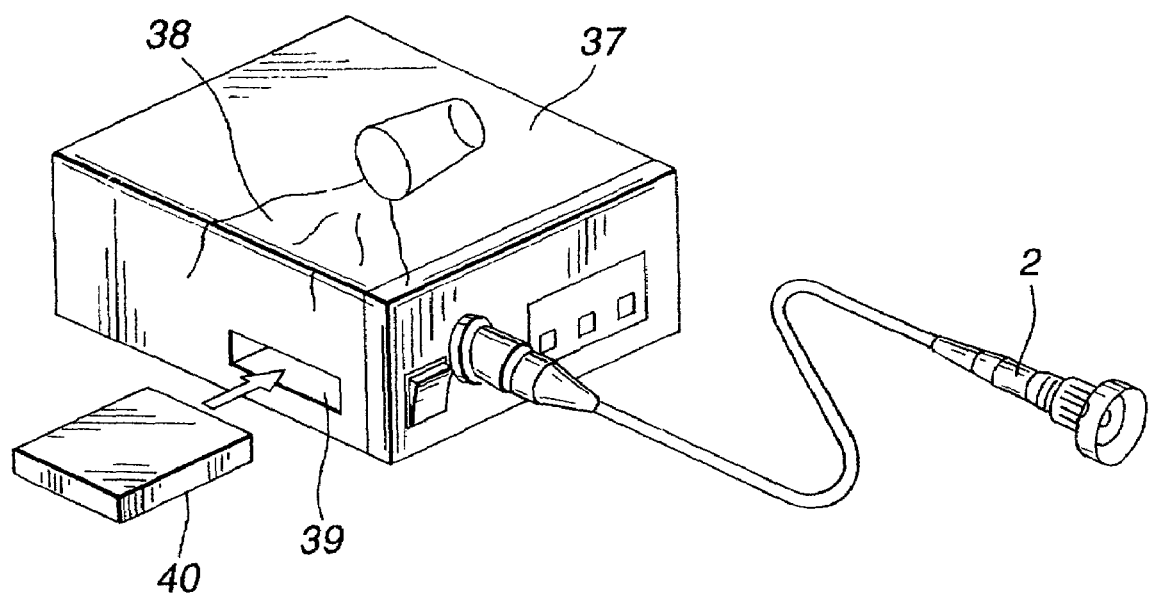
FIG. 45 is an explanatory diagram for demonstrating a drawback of a conventional system that when liquid such as water is spilled over a CCU, the liquid invades into the interior of an expansion slot.

The conventional system does not have an anti-liquid invasion structure formed around an expansion slot. When liquid 38 such as water is split over a CCU 37 as shown in FIG. 45, the liquid invades into the interior of an expansion slot 39 in which an expansion unit 40 is mounted. This may invite a short circuit between electrical contacts or corrosion in the CCU.

For improving the safety of medical equipment including a CCU with an expansion slot, the expansion slot is provided with an anti-liquid invasion means. An example of a structure including the anti-liquid invasion means will be described as another embodiment.

Figure 4:
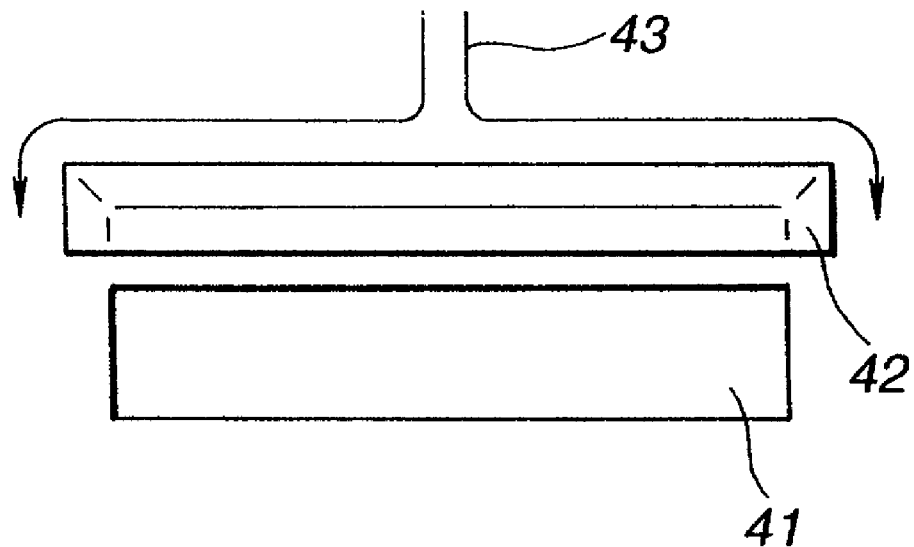
FIGS. 4 and 5 relate to a second embodiment of the present invention.
Figure 5:
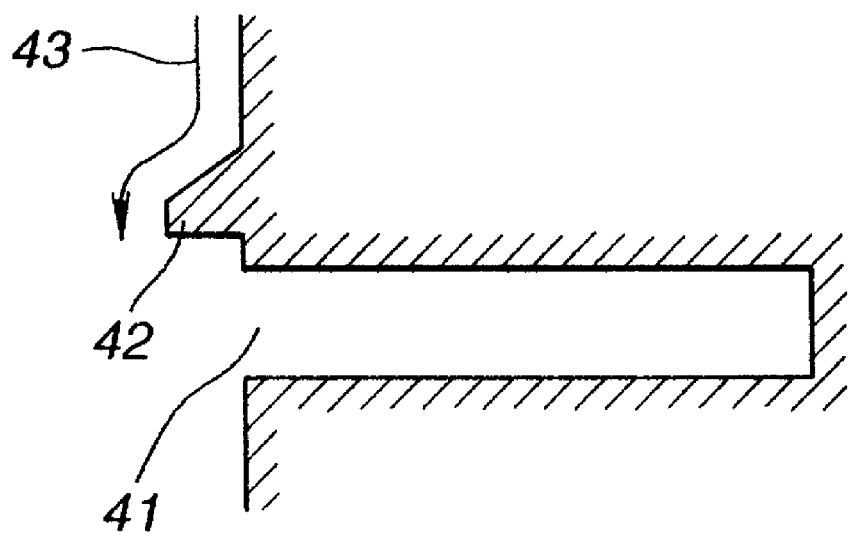

FIGS. 4 and 5 show a structure of an expansion slot in accordance with a second embodiment of the present invention. FIG. 4 is a front view and FIG. 5 is a sectional view.

An eaves-like projection 42 is formed on the upper margin of the opening of an expansion slot 41 formed in the face or lateral side of a CCU 5 over a range wider than the width of the opening. Liquid that has been split over the top of the CCU because of user's carelessness and flowing down will be blocked by the projection 42 as indicated with an arrow 43. The liquid will not invade directly into the expansion slot 41.

According to the second embodiment, invasion of liquid into the expansion slot can be prevented by a simple structure. Thus, the fear of causing a short circuit between electrical contacts and corrosion in the CCU, can be eliminated.

Figure 6:
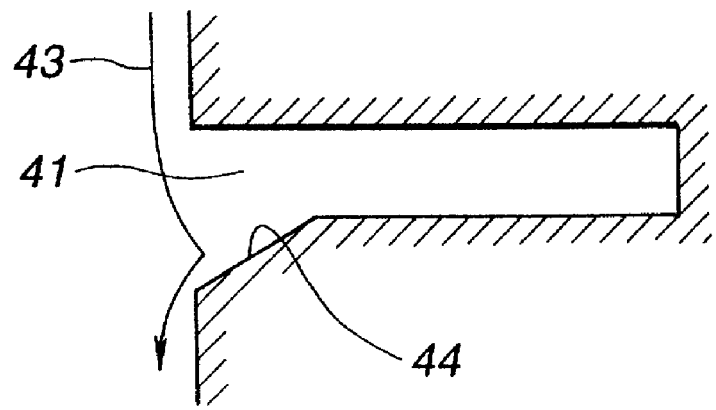
FIGS. 6 and 7 relate to a third embodiment of the present invention.
Figure 7:
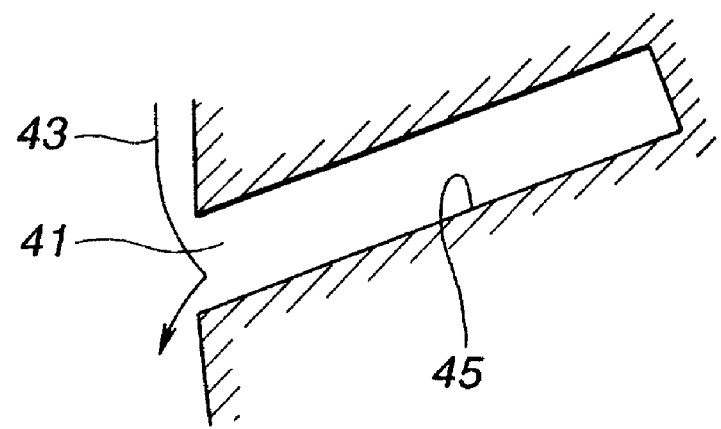

Third Embodiment:

In a third embodiment, as shown in FIG. 6, a slope 44 is formed as part of an inner lower surface of an expansion slit 41 near the opening of the expansion slot. Owing to the slope 44, invasion of liquid into the expansion slot can be prevented as indicated with an arrow 43. Moreover, in a variant shown in FIG. 7, the whole expansion slot 41 may be formed on a slope 45. The same operation and advantage as those mentioned above can still be exerted.

According to the third embodiment, another member such as an eaves-like projection need not be formed.

As with the second embodiment, invasion of liquid into the expansion slot can be prevented with a simple structure.

Fourth Embodiment:

The fourth embodiment is an example of a structure of an expansion slot having an anti-liquid invasion means and a shield means for shielding unnecessary radiative electromagnetic waves for attaining electromagnetic compatibility (EMC).

A housing case 51 of a CCU is made of a conducting material, thus realizing a shield structure against unnecessary electromagnetic waves radiated from the interior of the CCU. As shown in the sectional view of FIG. 8 and the diagram showing components to be assembled of FIG. 10, the housing case 51 has a case opening 53 bored for detachably attaching the expansion unit 52 shown in FIG. 9. A unit mount 54 into which an expansion unit 52 is fitted during mounting of the expansion unit is formed in the case opening 53. A contact connector 55 that is electrically coupled with the expansion unit 52 when the expansion unit is mounted and that transfers an electrical signal or the like to or from the expansion unit 52 is formed at the interior end of the unit mount 54.

A contact member 56 is sandwiched between the housing case 51 near the case opening 53 and the unit mount 54 so that the contact member 56 will be electrically coupled with the housing case 51. The portion of the contact member 56 bordered by the upper side and lateral sides of the case opening 53 is exposed in the opening to form a contact portion 56a. A hinge member 57 realized with a conductive member made of a metal or conducting rubber is located on the lower side of the case opening 53. One extreme portion of the hinge member 57 is fixed as a stationary portion 57a so that the portion will be electrically coupled with the housing case 51. The other extreme portion of the hinge member 57 can be opened or closed as a lid portion 58. The lid portion is constrained to move in a direction (direction of an arrow A in FIG. 8), in which it meets the contact portion 56a on the upper side of the case opening 53, by means of a spring member 59 attached to the hinge member 57.

Furthermore, the portion of the inner lower surface of the unit mount 54 inside the hinge member 57 is formed as a slope 60 opening toward the outside of the housing case 51.

Figure 9:
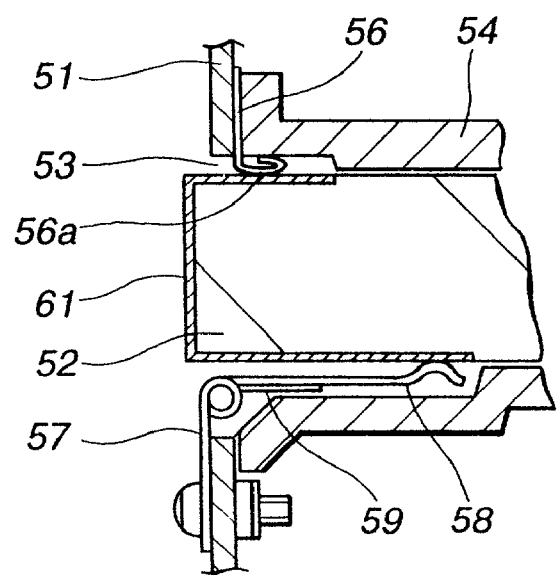
Figure 10:
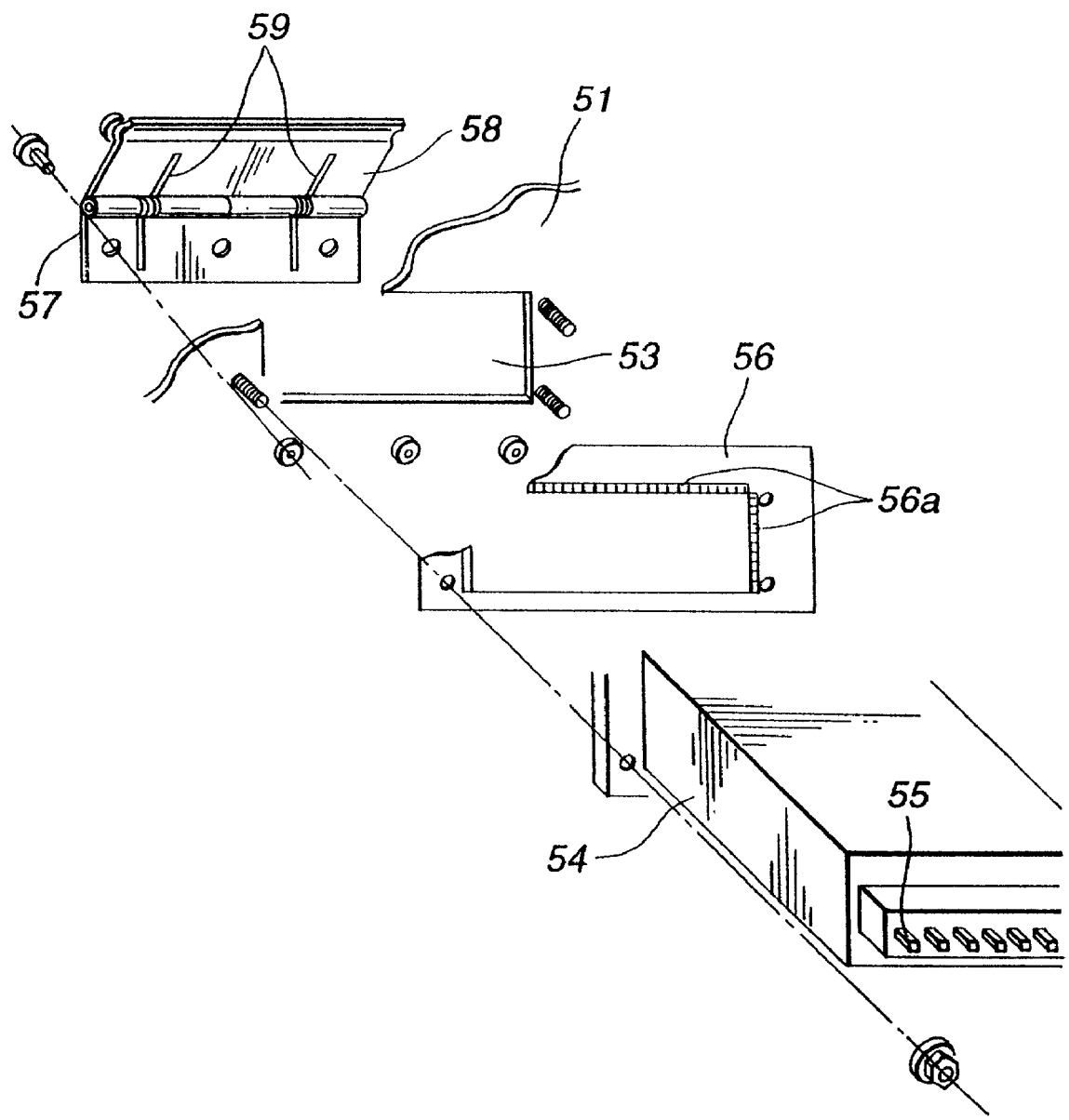
Figure 11:
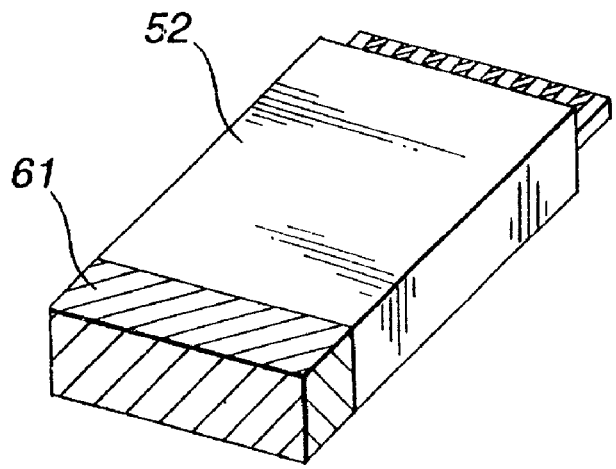
Figure 12:
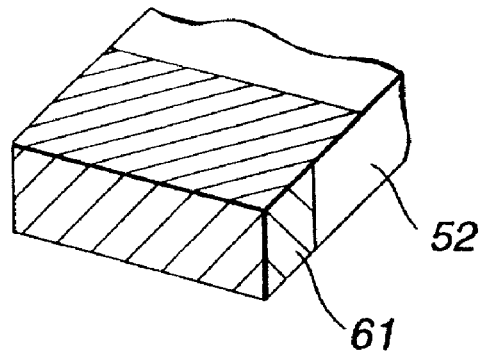

The expansion unit 52 has, as shown in FIGS. 11 and 12, a conductor 61. The conductor 61 is realized with a conductive member coated over the circumferential surfaces of a back portion of the expansion unit 52 which remains at least partially exposed when the expansion unit is inserted into the expansion slot. When the expansion unit 52 is mounted in the expansion slot, as shown in FIG. 9, the contact portion 56a of the contact member 56 over the upper side and lateral sides of the case opening meets the conductor 61 extending over the upper and lateral surfaces of the expansion unit 52. An end of the lid portion 58 of the hinge member 57 meets the portion of the conductor 61 over the lower surface of the expansion unit 52. This causes the lid portion 58 to conduct.

Figure 13:
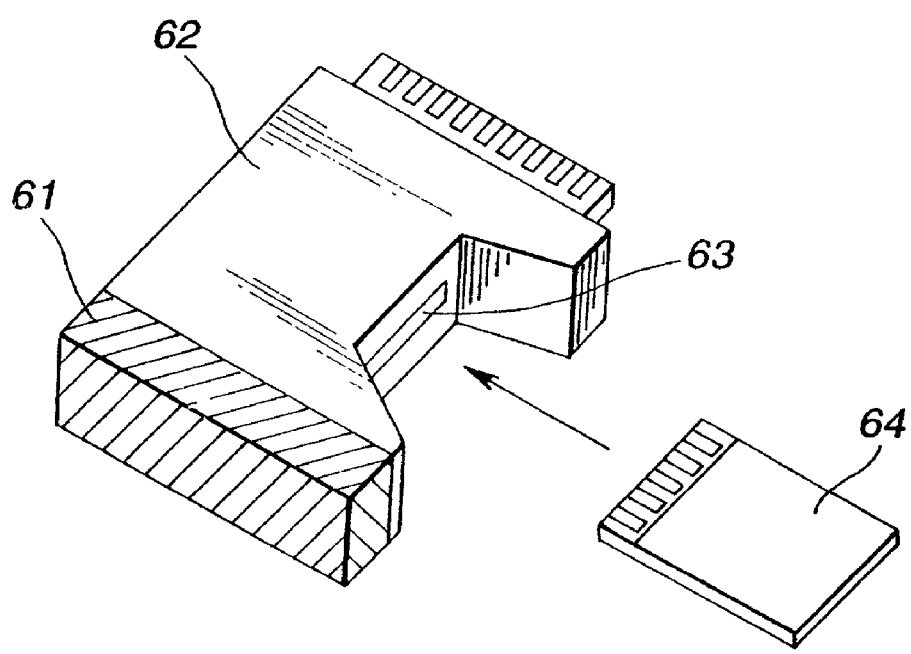

FIG. 13 shows a variant of the expansion unit 52. An expansion unit 62 of the variant has a card slot 63 formed in a lateral surface thereof. A memory card 64 such as a PC card can be mounted in the card slot. Like the structure shown in FIG. 11, a conductor 61 is formed on the back portion of the expansion unit that remains at least partially exposed when the expansion unit is inserted.

Figure 8:
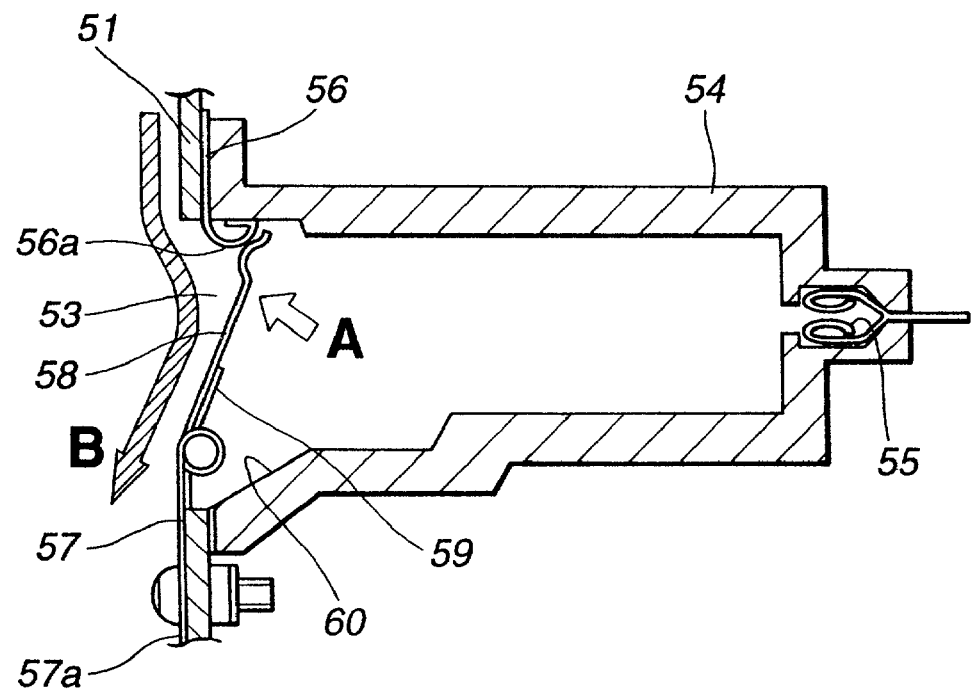
FIGS. 8 to 16 relate to a fourth embodiment of the present invention.

When the expansion unit 52 is not mounted in the thus-formed expansion slot, the lid portion 58 of the hinge member 57 is constrained to move in the direction of an arrow A in FIG. 8 by means of the spring member 59. This causes the lid portion 58 to meet the contact portion 56a of the contact member 56 to thus permit electrical conduction therebetween. The lid portion 58 is positioned to block the case opening 53. Thus, the lid portion 58 of the hinge member 57 fills the role of a lid for covering the case opening 53. Liquid flowing in from, for example, the top of the housing case 51 will flow along an arrow B in FIG. 8 but will not invade directly into the interior of the unit mount 54. Moreover, liquid invading into the interior of the housing case 51 through a gap in the hinge member 57 can be prevented from invading into the interior of the unit mount 54 owing to the slope 60 of the unit mount 54.

Moreover, when the expansion unit 52 is mounted, the conductor 61 on the expansion unit 52, the contact portion 56a of the contact member 56, and the end of the lid portion 58 of the hinge member 57 meet, as shown in FIG. 9, to form an electrically conductive path. This disables shielding, which is intended to attain EMC, of the case opening 53. Consequently, release of unnecessary radiative noises can be prevented. At this time, since the case opening 53 is blocked by the expansion unit 52, liquid can be prevented from invading into the interior of the unit mount 54 in the same manner as that when the expansion unit is not mounted.

Figure 14:
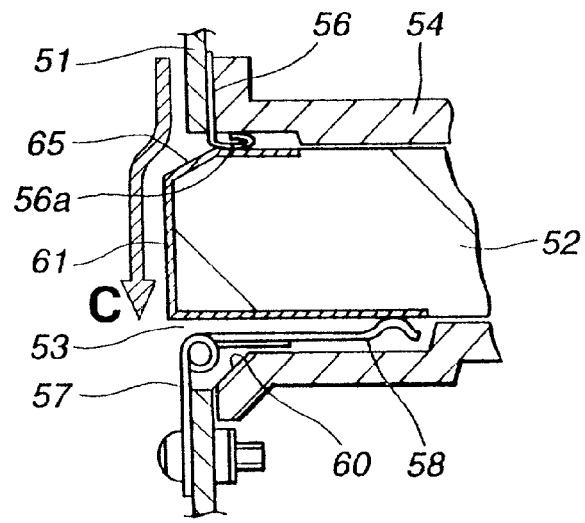

FIG. 14 shows a first variant of the expansion slot of the fourth embodiment. The first variant has such a structure that a slope 65 is formed on a back portion of the expansion unit 52 that remains exposed outside the housing case 51 when the expansion unit is inserted. Owing to the slope 65, even when the expansion unit 52 is mounted, liquid flowing down from the top of the housing case 51 flows in the direction of arrow C in FIG. 13. This structure can therefore prevent invasion of liquid into the interior of the unit mount 54 more reliably than the structure shown in FIG. 9.

Figure 15:
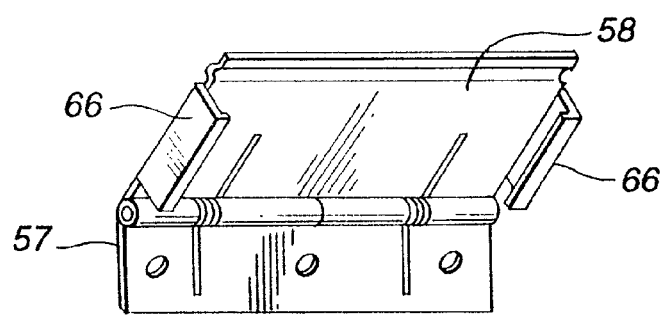

FIG. 15 shows a second variant of the expansion slot of the fourth embodiment. The second variant has such a structure that bent parts 66 are formed as parts of lateral ends of the lid portion 58 of the hinge member 57. Owing to the bent parts 66, the lateral sides of the case opening 53 can meet the contact member 56 more reliably. This leads to improved effects of preventing invasion of liquid and of shielding.

Figure 16:
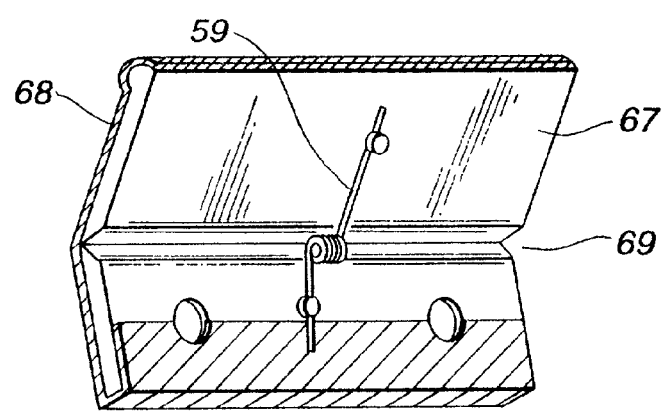

FIG. 16 shows a third variant of the expansion slot of the fourth embodiment. The third variant has such a structure that a lid member 67 is formed with a resin member which is bent in the middle to substitute for the hinge member 57. A metallic film 68 is bonded to the surface of the lid member 67. Owing to the lid member 67, a mechanical gap is not created along hinge 69. Consequently, an effect of preventing invasion of liquid can be exerted more efficiently.

As mentioned above, according to the fourth embodiment, an expansion slot can be realized to have both an anti-liquid invasion structure for preventing invasion of liquid into the expansion slot and a shield structure of achieving shielding for attaining EMC. This results in improved safety of medical equipment including a CCU having the expansion unit.

The adaptation of the endoscopic imaging system of this embodiment is not limited to an endoscope system for surgery in which a camera head is mounted on a rigid endoscope as described in conjunction with the previous embodiments. The endoscopic imaging system of this embodiment can also be adapted to an endoscope system for internal medicine in which a camera head is mounted on a soft endoscope or an electronic endoscope having an imaging device incorporated therein.

Moreover, a PC card is not limited to a card having a memory incorporated therein. A card to which a compact memory card such as a smart medium can be detachably attached, or a card having a compact hard disk incorporated therein can also be employed. Even when any expansion unit other than the PC card is mounted in an expansion slot, the structure of the expansion slot can be adapted to the aforesaid embodiments.

Fifth Embodiment:

(Configuration)

Figure 17:
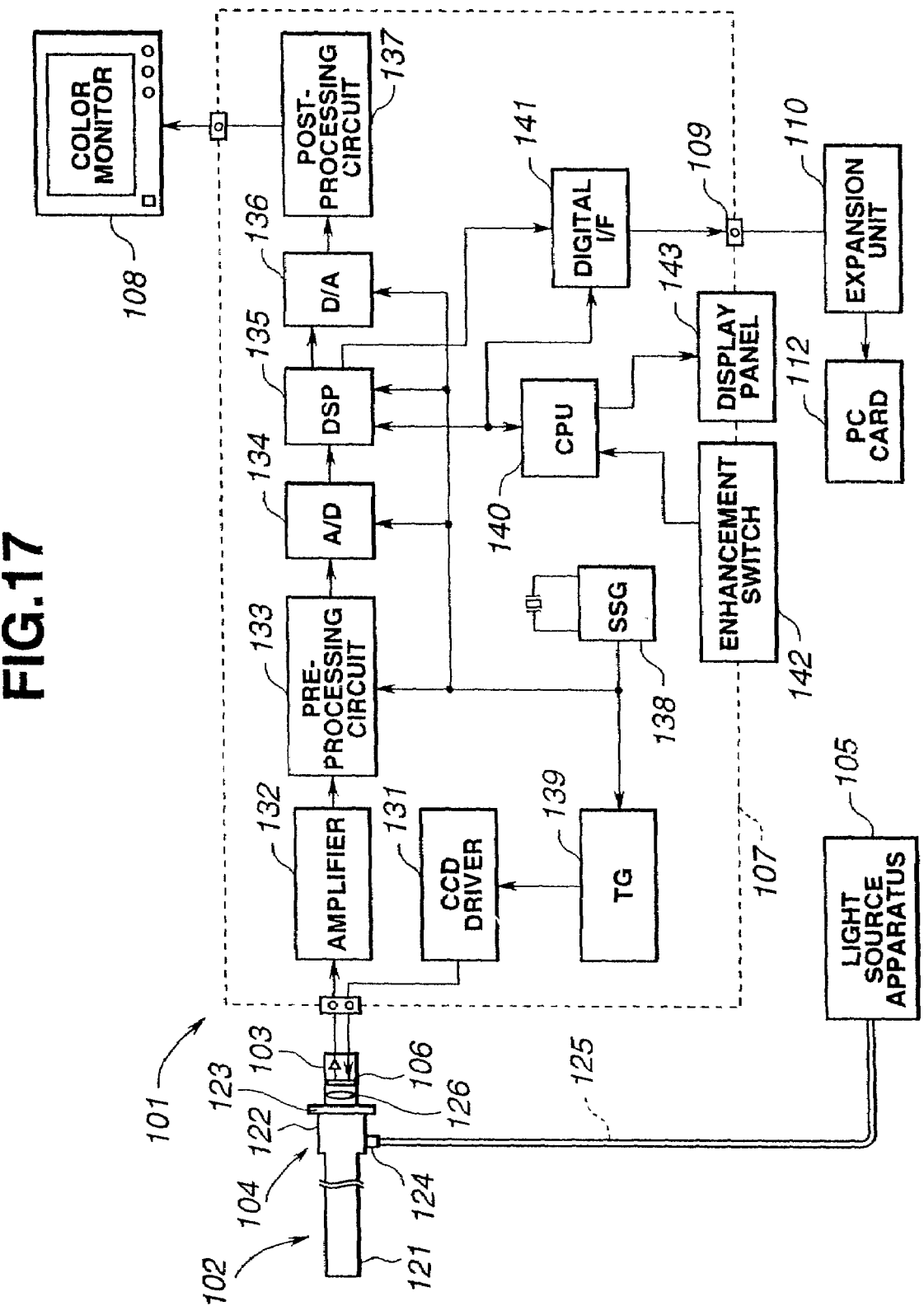
FIGS. 17 to 20 relate to a fifth embodiment of the present invention.
Figure 18:
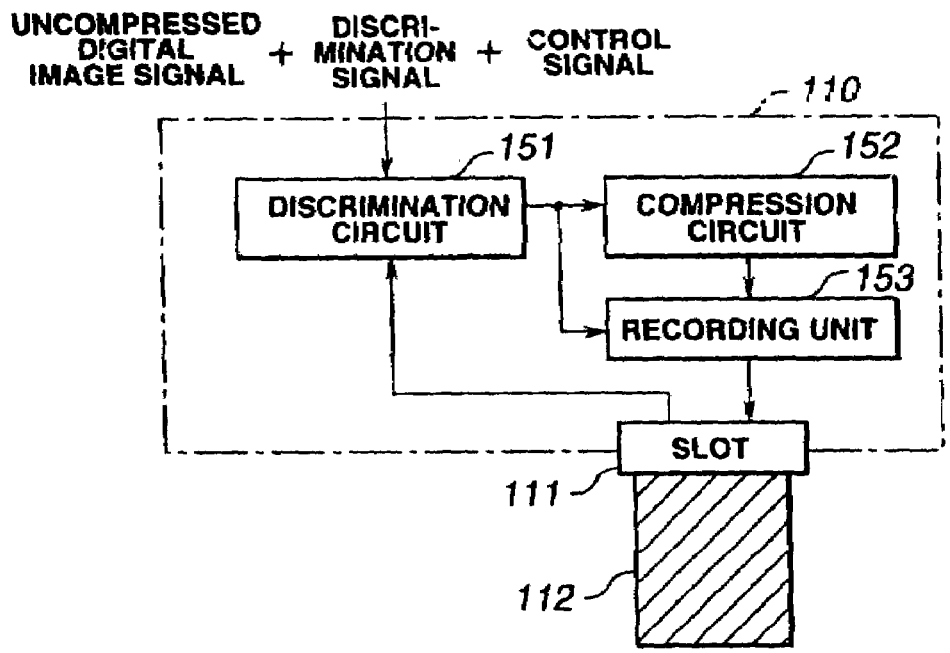

As shown in FIG. 17, an endoscopic imaging system 101 of this embodiment comprises a TV camera-mounted endoscope 104 having a TV camera 103 mounted on a rigid endoscope 102, a light source apparatus 105 for supplying illumination light to the rigid endoscope 102, a camera control unit (CCU) 107 for processing a signal sent from a charge-coupled device (CCD) that is a solid-state imaging device incorporated in the TV camera 103, a color monitor 108 for displaying an endoscopic image represented by a video signal output from the CCU 107, and an expansion unit 110 to be freely detachably plugged into a digital video output terminal 109 formed in the CCU 107. As shown in FIG. 18, a recording medium can be connected to the expansion unit 110. For example, a PC card 112 serving as a recording medium can be freely detachably connected to a PC card slot 111.

As shown in FIG. 17, the rigid endoscope 102 includes an elongated insertion unit 121, a hand-held unit 122 formed at the proximal end of the insertion unit 121, and an eyepiece unit 123 formed at the proximal end of the hand-held unit 122. The hand-held unit 122 has a light guide base 124, and is connected to the light source apparatus 105 over a light guide cable 125.

Illumination light emanating from a lamp in the light source apparatus 105 is converged by a condenser, and supplied to an incident end surface of a light guide in the light guide cable 125. The illumination light is emitted forward through the distal end surface of the light guide fitted in an illumination window located at the distal end of the insertion unit 121 over the light guide lying through the rigid endoscope 102. Thus, an object such as a lesion is illuminated.

Moreover, an objective lens is fitted in an observation window adjacent to the illumination window located at the distal end of the insertion unit 121. The objective lens forms an objective image at an image formation position. The formed image is transmitted by a system of relay lenses that are arranged in the insertion unit 121 and opposed to the objective lens. The image is then re-formed near the eyepiece unit 123. The image is then re-formed on the CCD 106 by an eyepiece lens included in the eyepiece unit 123, and an image formation lens 126 included in the TV camera 103 and opposed to the eyepiece lens.

Incidentally, a mosaic filter that is not shown is located in front of the image plane (photoelectric conversion plane) of the CCD 106. Color components of light incident on each pixel are optically separated from one another. That is to say, an imaging means of this embodiment is a simultaneous imaging means for acquiring a color image signal under white illumination light.

The CCD 106 of the TV camera 103 is connected to the CCU 107. A CCD driving signal is applied from a CCD driver 131 in the CCU 107 to the CCD 106, and photoelectrically converted into a CCD output signal (image signal). The CCD output signal is then input to an amplifier 132 in the CCU 107. The signal amplified by the amplifier 132 is input to a pre-processing circuit 133.

The CCD output signal input to the pre-processing circuit 133 is pre-processed by performing correlation doubling sampling (CDS) and sample-and-hold (S/H). The resultant signal is then input to an A/D converter 134 and converted into a digital signal. The digital signal is input to a digital signal processor (DSP) 135.

The DSP 135 recomposes the input digital signal according to the line-sequential system. Consequently, three digital signals Y, Cr, and Cb propagating through different channels are separated from one another, and then converted into an RGB digital signal according to a matrix conversion formula. The RGB digital signal resulting from the matrix conversion has the white balance or black balance thereof adjusted. Thereafter, the resultant signal is digitally processed by performing enhancement, gamma correction, and character convolution, and then input to a D/A converter 136.

The digital signal input to the D/A converter 136 is converted into an analog signal, converted into a standard video signal by a post-processing circuit 137, and then output to a color monitor 108.

Moreover, the CCU 107 is provided with a reference signal generator (SSG) 138. Based on a clock signal generated by the SSG 138, a timing signal generator (TG) 139 generates a timing signal. The CCD driver 131 drives the CCD 106 in response to the timing signal. The clock signal sent from the SSG 138 is also output to the pre-processing circuit 133, A/D converter 134, DSP 135, and D/A converter 136. The CCD output signal (image signal) sent from the CCD driver 131 is processed synchronously with the clock signal.

Moreover, a digital video signal sent from the DSP 135 is output to a digital interface 141 under the control of the CPU 140. The digital interface 141 appends a control signal sent from the CPU 140 and a discrimination signal that will be described later to the digital video signal, and outputs a resultant signal to the expansion unit 110. Moreover, an enhancement switch 142 and a display panel 143 are connected to the CPU 140. By handling the enhancement switch 142, a magnitude of enhancement to be achieved by the DSP 135 can be specified.

The discrimination signal to be appended to the digital video signal by the digital interface 141 indicates the number of pixels and angular field of view permitted by the CCD 106 in the TV camera 103, and a set value of the enhancement switch 142. The CPU 140 allows the DSP 135 to read these parameters and output them to the digital interface 141. Moreover, the parameters are displayed on the display panel 143.

As shown in FIG. 18, the expansion unit 110 includes a discrimination circuit 151 for inputting an uncompressed digital video signal, to which a discrimination signal is appended by the digital interface 141, extracting the discrimination signal, appending to the uncompressed digital video signal a compressibility signal proportional to the discrimination signal, and outputting the resultant digital video signal. The expansion unit 110 further includes a compression circuit 152 for compressing an uncompressed digital video signal, to which the compressibility signal sent from the discrimination circuit is appended, at a level of compressibility indicated by the compressibility signal, and a recording unit 153 for recording the compressibility signal and digital video signal on a PC card 112 via a PC card slot 111.

The PC card 112 is divided into segments associated with a plurality of data groups, for example, patients or medical fields. Associated patient data items and medical-field data items are recorded in the segments. The discrimination circuit 151 can select a level of compressibility according to patient data or medical-field data recorded on the PC card 112, and provide a discrimination signal indicating the level of compressibility.

(Operation)

Next, the operation of the endoscopic imaging system 101 of this embodiment having the foregoing components will be described.

For example, when the abdomen is operated under endoscopic observation, the TV camera 103 is mounted on the rigid endoscope 102 and connected to the light source apparatus 105 and CCU 107. The color monitor 108 is connected to the CCU 107. Moreover, the expansion unit 110 is plugged into the digital video output terminal 109 of the CCU 107. The PC card 112 is connected to the PC card slot 111 of the expansion unit 110.

The insertion unit 121 of the rigid endoscope 102 is thrust into the patient's abdomen by piercing the abdominal wall using a trocar and cannula. Thus, an organ in the abdomen can be observed. An (endoscopic) image of the organ is displayed on the color monitor 108. An operator views the image. When an image the operator wants to record is displayed on the color monitor 108, the operator handles a hand release switch or foot switch that is not shown. Thus, an endoscopic image can be recorded on the PC card 112 in the same manner as photography. The recorded image can be utilized later by handling a personal computer or the like.

At this time, the CCD 106 of the TV camera 103 is driven synchronously with a clock signal sent from the SSG 138. The pre-processing circuit 133, A/D converter 134, and DSP 135 process a digital video signal synchronously with the clock signal.

Figure 19:
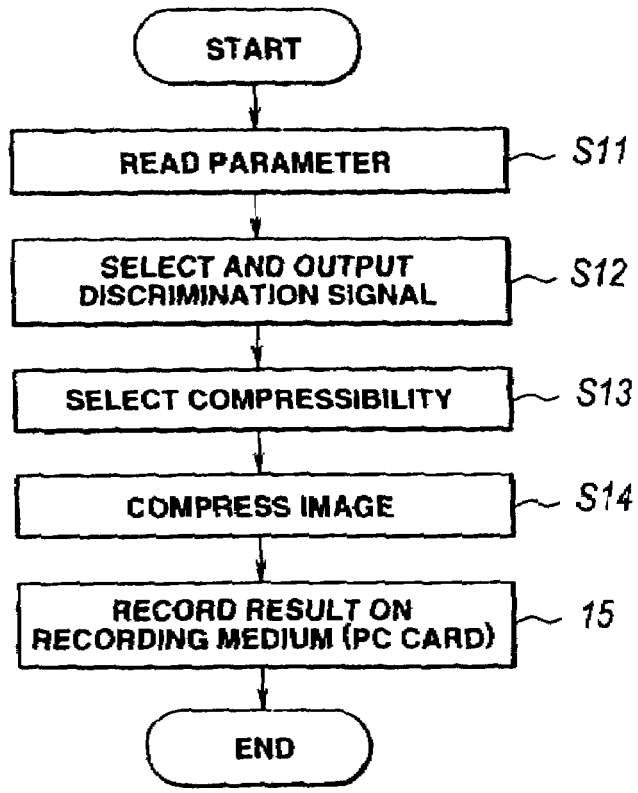

The CPU 140 receives, as shown in FIG. 19, a signal sent from the DSP 135 so as to read the number of pixels permitted by the CCD 106 as a parameter at step S11. At step S12, Table 1 is referenced in relation to the read number of pixels, and then a discrimination signal is output to the digital interface 141. The digital interface 141 appends the discrimination signal to a digital video signal sent from the DSP 135.

TABLE 1

| Parameter (Number of pixels) | Discrimination signal |
|---|---|
| 250 thousand pixels | 01 h |
| 410 thousand pixels | 02 h |
| 800 thousand pixels | 03 h |
| 3 CCD | 04 h |
| . | . |
| . | . |
| . | . |

Thereafter, at step S13, the discrimination circuit 151 in the expansion unit 110 reads the discrimination signal appended to the digital video signal. The discrimination circuit 151 then references Table 2 in relation to discrimination signal, and appends a compressibility signal to the digital video signal. The resulting digital video signal is then output to the compression circuit 152.

TABLE 2

| Discrimination signal | Compressibility |
|---|---|
| 01 h | a |
| 02 h | b |
| 03 h | c |
| 04 h | d |
| . | . |
| . | . |
| . | . |

Then, at step S14, the compression circuit 152 compresses the digital video signal at a level of compressibility indicated by the compressibility signal. At step S15, the recording unit 153 records the resultant digital video signal on the PC card 112 together with the compressibility signal via the PC card slot 111. Thus, the compressibility signal is recorded together with the compressed digital video signal on the PC card 112. The compressed image can therefore be decompressed properly by handling a personal computer or the like when it must be reopened.

The parameter used at step S12 in FIG. 19 is not limited to the number of pixels permitted by the CCD 106. Alternatively, the type of rigid endoscope 102 defined by an angular field of view permitted by the rigid endoscope may be used. In this case, the CPU 140 uses as a parameter any of a first endoscope, second endoscope, third endoscope, etc., which are sorted in that order from the smallest-diameter endoscope to the largest diameter one as shown in Table 3, to select a discrimination signal.

TABLE 3

| Parameter (Angular field of view) | Discrimination signal |
|---|---|
| First endoscope | 01 h |
| Second endoscope | 02 h |
| Third endoscope | 03 h |
| Fourth endoscope | 04 h |
| . | . |
| . | . |
| . | . |

Moreover, the parameter used at step S12 in FIG. 19 may be a set value of the enhancement switch 142. Based on the set value, Table 4 may be referenced for selection.

TABLE 4

| Parameter (Enhancement) | Discrimination signal |
|---|---|
| Level 1 | 01 h |
| Level 2 | 02 h |
| Level 3 | 03 h |
| Level 4 | 04 h |
| . | . |
| . | . |
| . | . |

Moreover, the discrimination signal to be read at step S13 in FIG. 19 may represent medical-field data as listed in Table 5 or patient data as listed in Table 6. Based on the data, the discrimination circuit 151 selects a level of compressibility.

The medical data or patient data may be recorded as data on the PC card 112 in advance. The discrimination circuit 151 may read the data to determine a level of compressibility.

TABLE 5

| Discrimination signal | Compressibility |
|---|---|
| General surgery | a |
| Urology | b |
| Otorhinology | c |
| Orthopedics | d |
| . | . |
| . | . |
| . | . |

TABLE 6

| Discrimination signal | Compressibility |
|---|---|
| Patient a | a |
| Patient b | b |
| Patient c | c |
| Patient d | d |
| . | . |
| . | . |
| . | . |

(Advantage)

As mentioned above, the endoscopic imaging system 101 of this embodiment makes it possible to change levels of compressibility automatically according to an endoscopic image for compressing image data, and then record resultant data on a recording medium such as the PC card 112. Consequently, the use efficiency of a recording area on the recording medium can be improved, and the load imposed on an operator during handling can be alleviated.

Figure 20:
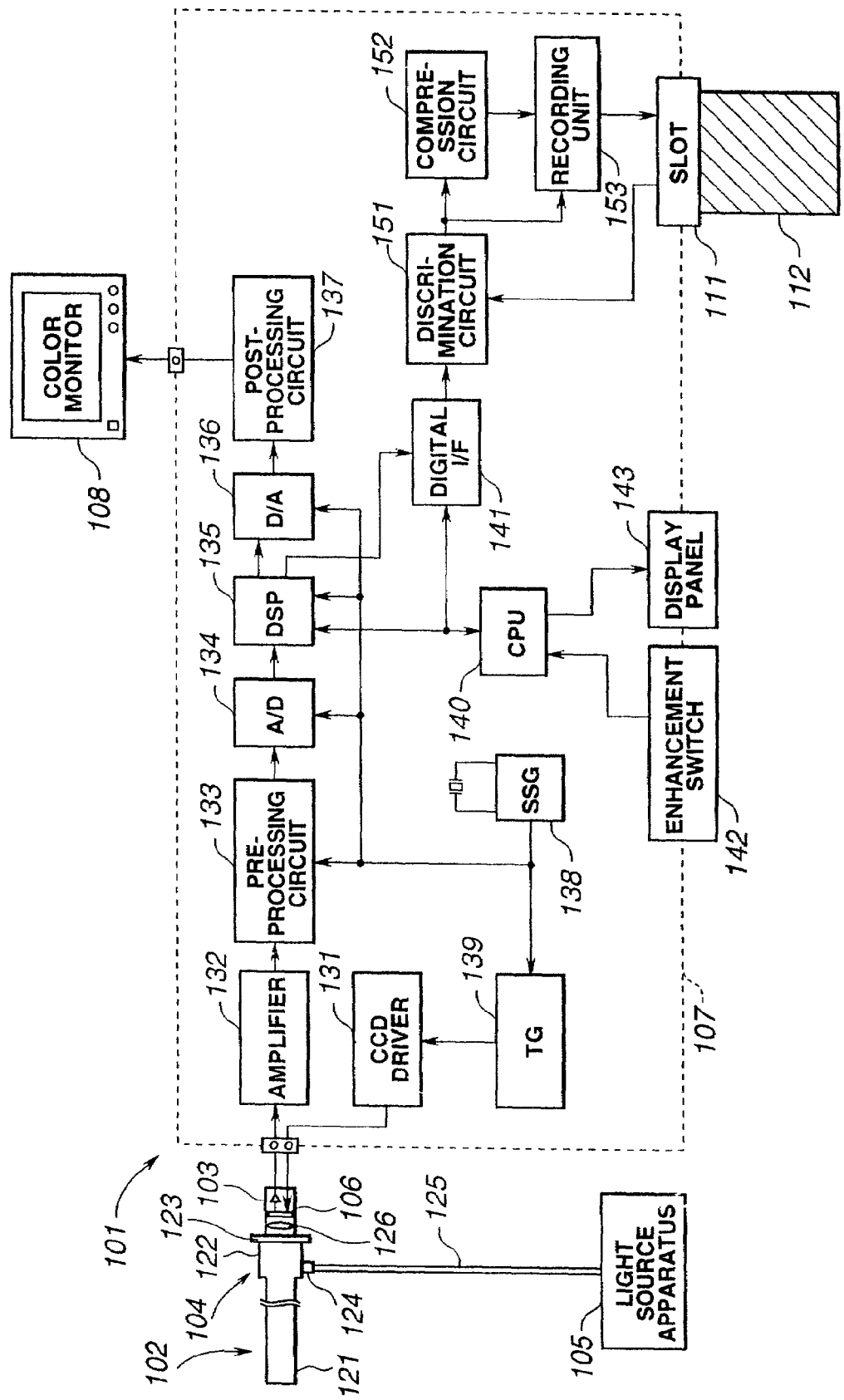

Incidentally, the expansion unit 110 may be formed with a PC card. Moreover, the structure of the expansion unit 110 may be, as shown in FIG. 20, included in the CCU 107.

Moreover, this embodiment has been described by taking the TV camera-mounted endoscope 104, which is the rigid endoscope 102 having the TV camera 103 mounted thereon, for instance. The embodiment is not limited to this type of endoscope. Alternatively, a TV camera-mounted soft endoscope, which is a soft endoscope having the TV camera mounted thereon, or an electronic endoscope having a CCD incorporated in a distal part of an insertion unit thereof may be used in connection with this embodiment.

Figure 21:
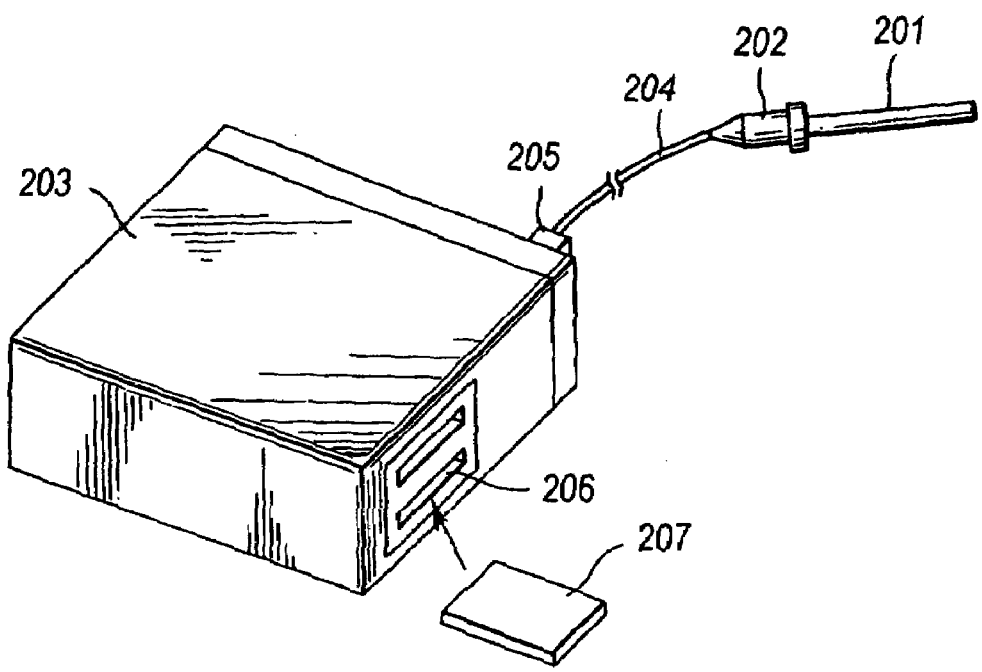
FIGS. 21 to 29 relate to a sixth embodiment of the present invention.

Sixth Embodiment:

An endoscopic imaging system of this embodiment comprises, as shown in FIG. 21, a camera head 202 to be mounted on, for example, a rigid endoscope 201 for surgery, and a camera control unit (hereinafter a CCU) 203 for processing a video signal representing an object image projected by the camera head 202. A signal cable 204 is extending from the camera head 202. The camera head 202 is connected to the CCU 203 via a connector 205 attached to an end of the signal cable 204. A card slot 206 is formed in a lateral side of the CCU 203. A memory card 207 in which set data or the like that will be described later is stored can be inserted into the card slot 206.

Figure 22:
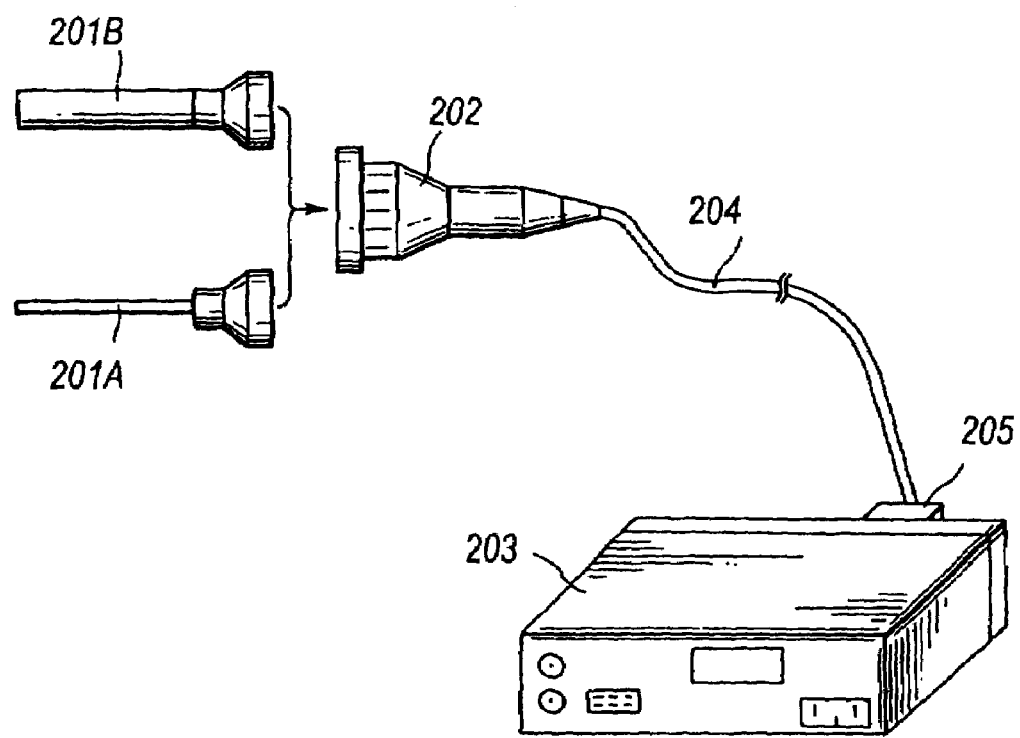

A plurality of endoscopes can be, as shown in FIG. 22, connected to the camera head 202. For example, a small-diameter scope 201a employed in the field of urology or the like, a large-diameter scope 201b used as a laparoscope or the like, and any other endoscope having different specifications can be alternately mounted for use on camera head 202.

Figure 23:
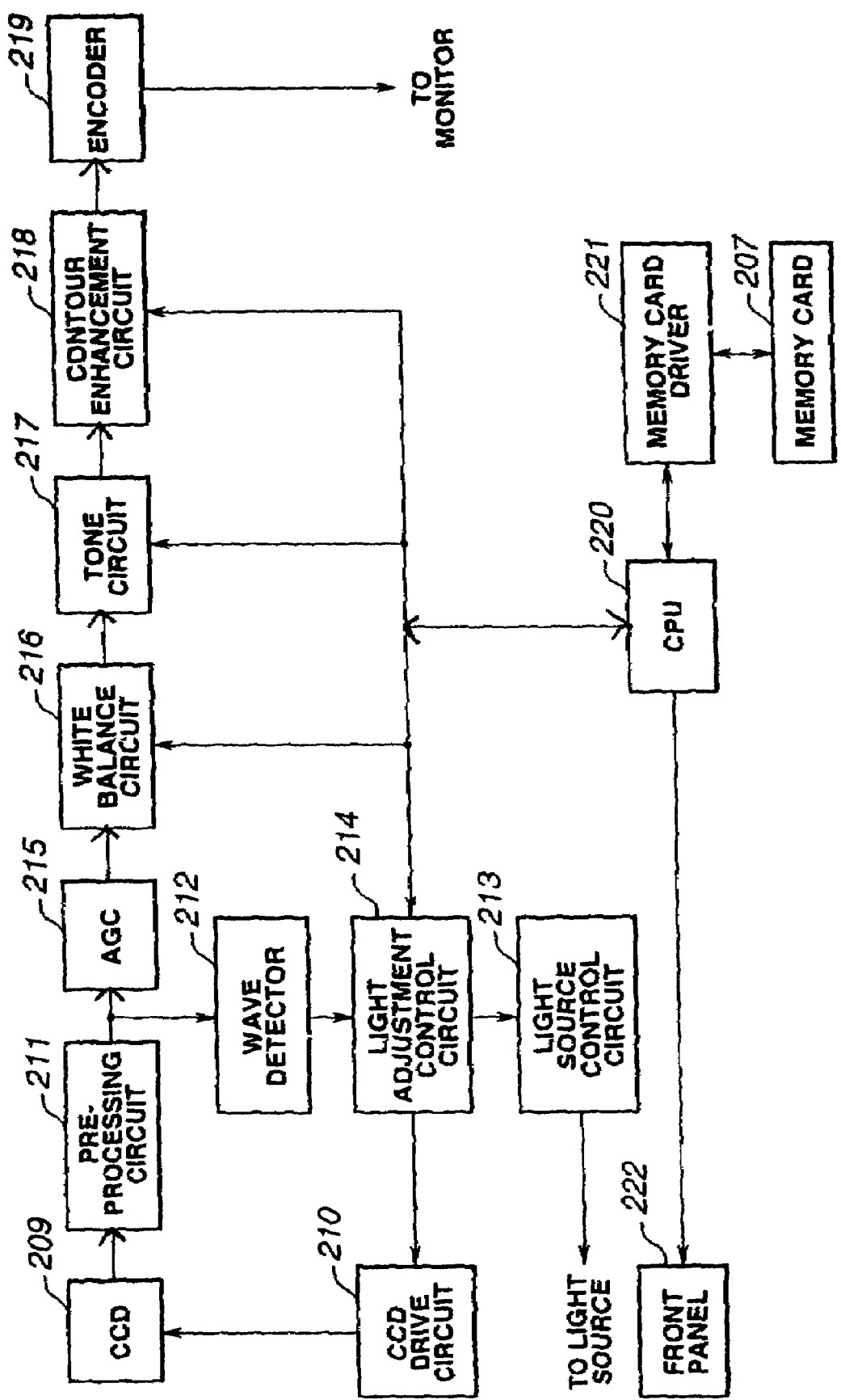

The CCU 203 includes, as shown in FIG. 23, a CCD drive circuit 210 for driving a CCD 209 that is an imaging device incorporated in the camera head 202, a pre-processing circuit 211 for pre-processing a signal output from the CCD 209, a wave detector 212 for detecting the waveform of an output of the pre-processing circuit 211, a light adjustment control circuit 214 for sending a control signal to the CCD drive circuit 210 and a light source control circuit 213 for controlling an amount of light emanating from a light source, which is not shown, so as to adjust light. On the succeeding side of the pre-processing circuit 211, there are an AGC circuit 215 for controlling a gain automatically, a white balance circuit 216 for adjusting the white balance of an output image, a tone circuit 217 for adjusting the tone of an output image, a contour enhancement circuit 218 for enhancing the contour of an output image, and an encoder 219 for converting a video signal into a standard video signal. Thus, a video signal representing an object image is output to a monitor that is not shown.

Moreover, the CCU 203 is provided with a CPU 220 for controlling the light adjustment control circuit 214, white balance circuit 216, tone circuit 217, and contour enhancement circuit 218, a memory card driver 221 connected to the memory card 207 for driving the memory card 207 or transferring data to or from the memory card 207, and a front panel 222 having an indicator for indicating a setting for an operation and having operation switches arranged thereon.

Figure 24:
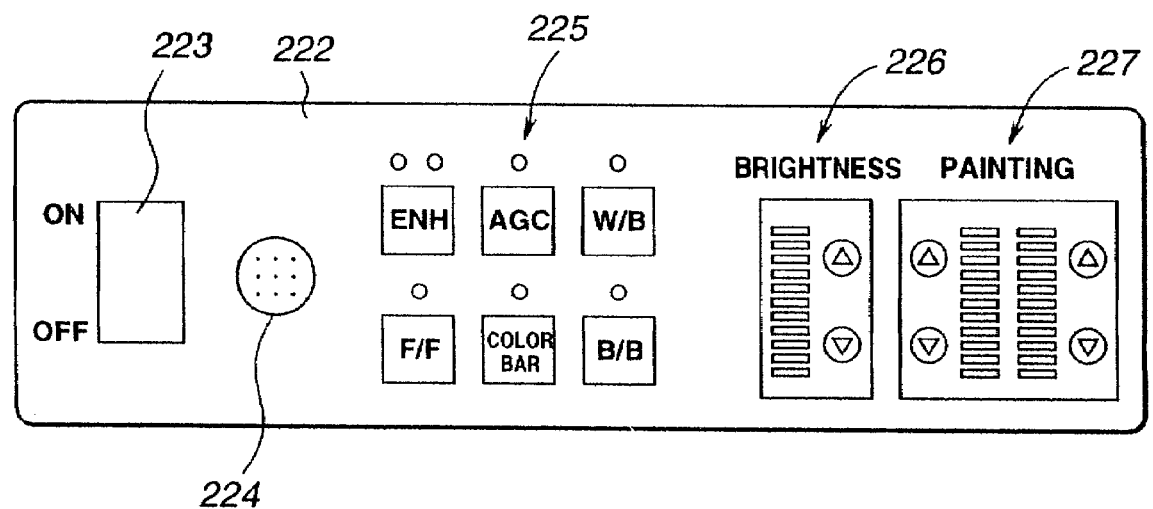

Arranged on the front panel 222 are, as shown in FIG. 24, a power switch 223, a connector receptor 224 into which the connector 205 of the camera head 202 is plugged, a group of operation switches 225 for use in instructing an operation such as white balance adjustment or contour enhancement, a luminance setting indicator 226 for indicating a set level of luminance for an output image, and a tone setting indicator 227 for indicating a set level of tone for an output image.

Next, the operation of the endoscopic imaging system of this embodiment will be described. In the endoscopic imaging system of this embodiment, a video signal representing an object image is photoelectrically converted by the CCD 209 in the camera head 202, and then input to the CCU 203. The pre-processing circuit 211, AGC circuit 215, white balance circuit 216, tone circuit 217, contour enhancement circuit 218, and encoder 219 incorporated in the CCU 203 process the video signal. The object image is then displayed on the monitor, not shown in the figure. At this time, the wave detector 212 detects the waveform of an output of the CCD 209, and outputs a wave detection signal. Based on the wave detection signal, the light adjustment control circuit 214 controls the CCD drive circuit 210 and light source control circuit 213 to control light adjustment for adjusting the brightness of an image.

With a difference in field in which an endoscope is employed, the state of an object differs, and a way of displaying a produced image and the tone of the image differ correspondingly. Adjustment values including a white balance setting value, a tone setting value, a level of enhancement, and a frequency must therefore be varied depending on an object region to be observed. The settings for an operation must thus be attained properly.

Figure 25:
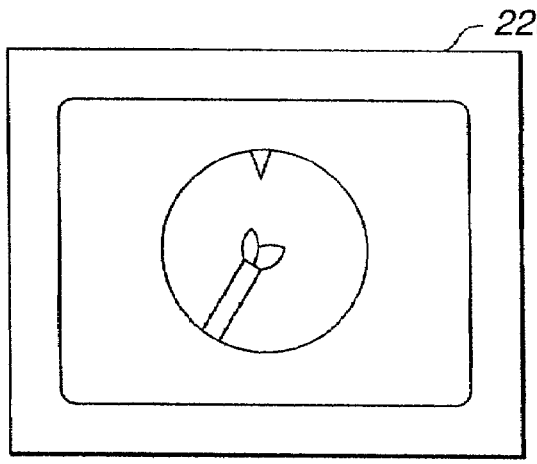
Figure 26:
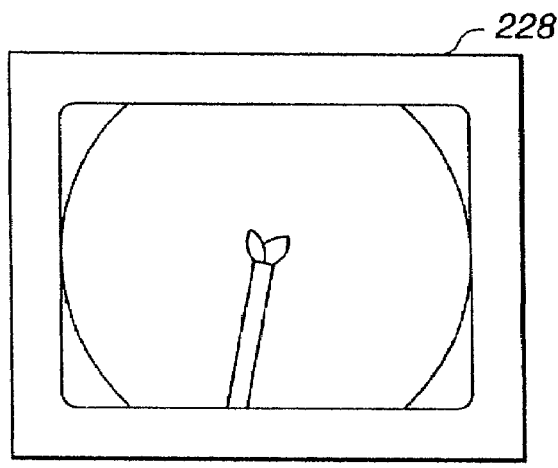

For example, for an examination or surgical procedure in the field of urology, the camera head 202 is mounted on the small-diameter scope 201a in order to visualize an object. The object image is, as shown in FIG. 25, displayed in part of the center of the monitor screen on the monitor 228. For the field of surgery using a laparoscope, the camera head 202 is mounted on the large-diameter scope 201b in order to visualize an object. The object image is, as shown in FIG. 26, displayed in substantially the whole of the monitor screen.

In this embodiment, a memory card 207 in which appropriate adjustment values are stored is prepared for each object field. When the endoscopic imaging system is put to use, the camera head 202 is mounted on an associated endoscope 201, and a memory card 207 associated with an intended field is inserted into the card slot 206. The CPU 220 reads setting data which represent the adjustment values stored in the memory card 207, via the memory card driver 221. The CPU 220 then sends a control signal to each of the light adjustment control circuit 214, white balance circuit 216, tone circuit 217, and contour enhancement circuit 218. Thus, various adjustment values are modified.

Figures 27, 29:
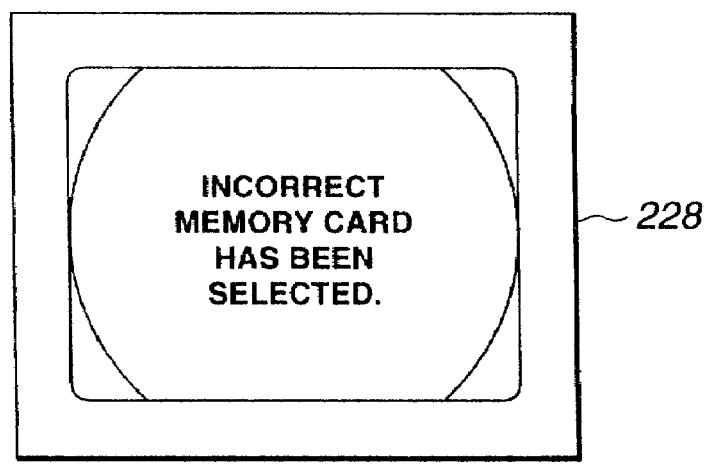

FIG. 27 shows an example of setting data representing adjustment values in relation to object fields. For the field of urology or for the field using an arthroscope, the adjustment values are specified in order to attain a low speed of light adjustment, a low level of light adjustment, a bluish level of tone, and a high degree of contour enhancement. Moreover, for the field using a laparoscope, the adjustment values are specified in order to attain a high speed of light adjustment, a high level of light adjustment, a reddish level of tone, and a low degree of contour enhancement.

For the field of urology or for the field using an arthroscope, the picture size of an object image is small. The image tends to hunch or cause halation. The adjustment values are therefore specified in order to attain a speed of light that is lower than the one for the field using a laparoscope, and a lower level of light adjustment. A halogen light source is often adopted for the field of urology or for the field using an arthroscope, while a xenon light source is often adopted for the field using a laparoscope. Halogen light is more reddish than xenon light. For the field of urology or for the field using the arthroscope, tone is set to a bluish level. As for contour enhancement, since an object in the field of urology or the field using the arthroscope is often solely white, contour enhancement is set to a rather high level.

Since settings for operations of light adjustment control, tone adjustment and contour enhancement are thus modified, the endoscopic imaging system can be set to a state suitable for a particular object field by carrying out simple handling. Endoscopic observation can therefore be carried out in an optimal operational environment at all times.

Moreover, the endoscopic imaging system of this embodiment includes an alarm means for giving an alarm to a user when an incorrect memory card inconsistent with an intended object field is inserted. The operation of the alarm means will be described in conjunction with FIGS. 28 and 29.

Figure 28:
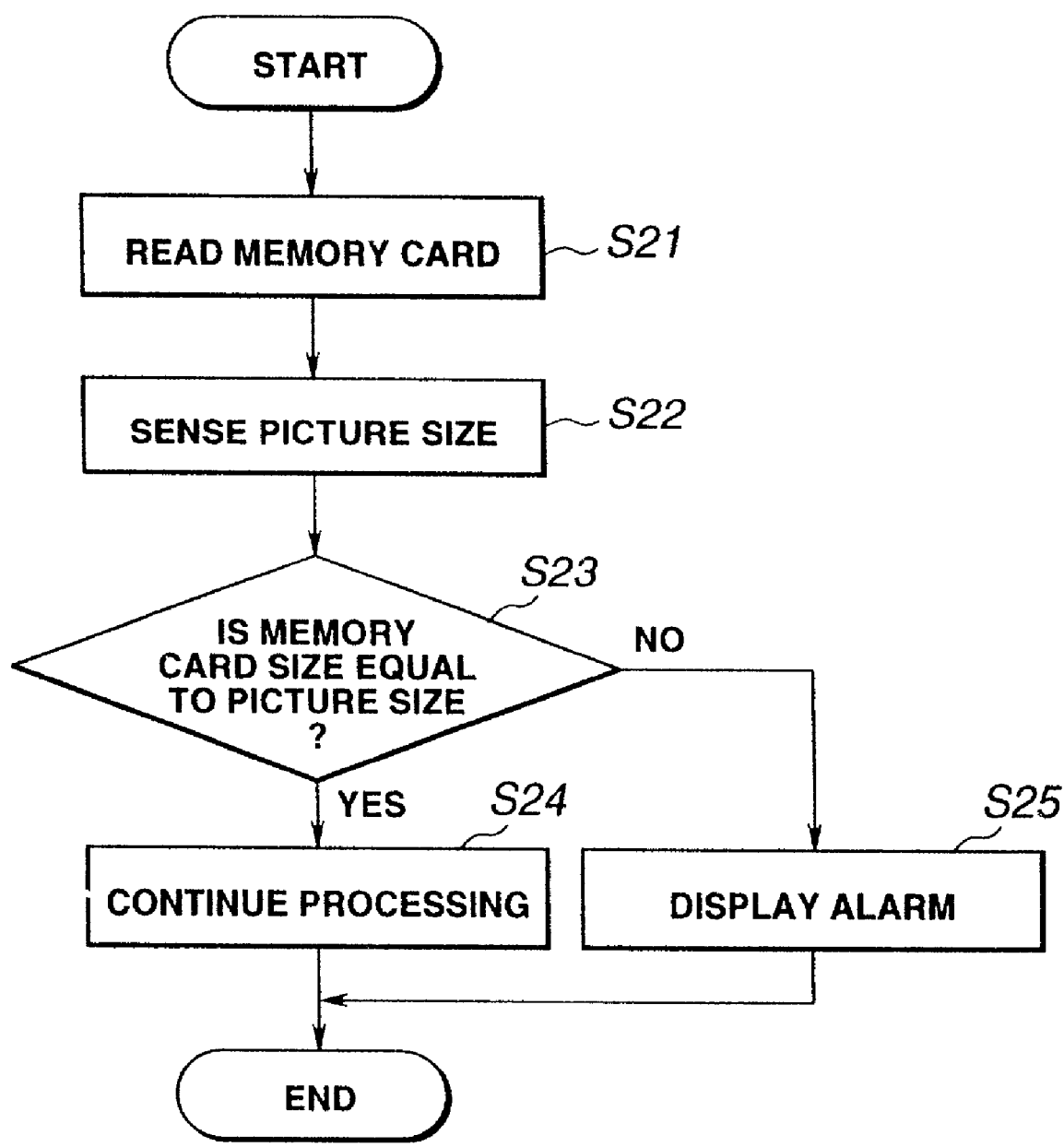

The CPU 220 in the CCU 203 reads, as described in the flowchart of FIG. 28, set data representing adjustment values from the memory card 207 inserted into the card slot 206 at step S21. At step S22, a picture size for an object image is sensed according to wave detection-related information represented by an image signal output from the CCD 209. At step S23, the wave detection-related information indicating the picture size for the object image is compared with object field information corresponding to the setting data stored in the memory card 207. It is then judged whether or not the picture size agrees with a picture size specified for an object field defined by the type of connected endoscope or a region to be observed.

If the picture size agrees with the picture size specified for the object field, it is judged that a correct memory card has been inserted. Control is then passed to step S24. Subsequent setting modification or the like is carried out. By contrast, if the picture size disagrees therewith, it is judged that an incorrect memory card has been inserted. Control is passed to step S25, whereupon an alarm display is carried out. The alarm display is, for example, such that an alarm having the contents shown in FIG. 29 is displayed in a screen of the monitor 228.

Owing to the alarm means, even when an incorrect memory card is inserted, a user can be informed of the fact and aware of incorrect use. A fear of establishing a setting state unintended by the user can be eliminated.

Figure 30:
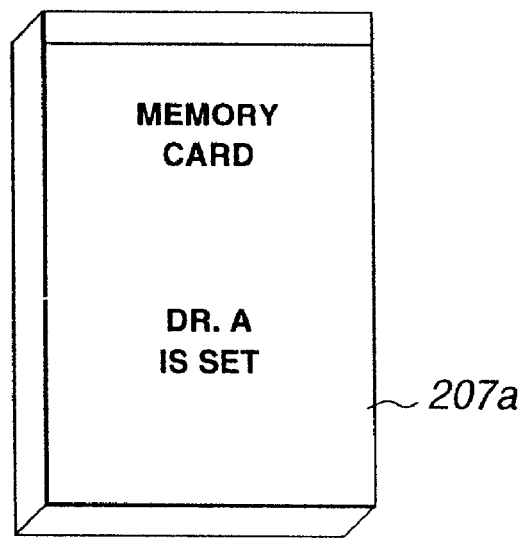
FIGS. 30 and 31 relate to a seventh embodiment of the present invention.
Figure 31:
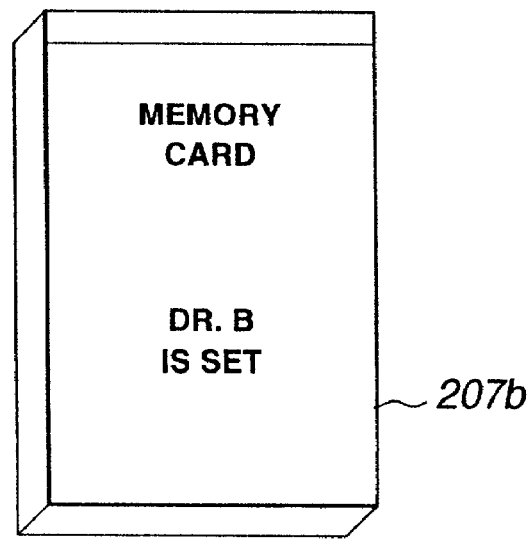

Seventh Embodiment:

The seventh embodiment is an example in which a memory card having proper adjustment values stored thereon is prepared for each doctor, and in which settings for various operations can be modified. A memory card 207a dedicated to Dr. A shown in FIG. 30 and a memory card 207b dedicated to Dr. B shown in FIG. 31 are made available. When either of the doctors uses the endoscopic imaging apparatus, his/her own memory card is inserted into the card slot 206 of the CCU 203. Like the sixth embodiment, settings for operations of light adjustment control, tone adjustment, and contour enhancement are modified so that desired adjustment values can be specified.

For example, assuming that Dr. A likes a bright and reddish image, setting data associated with such an image is stored on the memory card 207a. Specifically, the brightness of the image is set to a higher level and the tone thereof is set to a reddish level. Moreover, assuming that Dr. B likes a dark and bluish image setting data associated with such an image is stored on the memory card 207b. Specifically, the brightness of the image is set to a lower level and the tone thereof is set to a bluish level.

Figure 46:
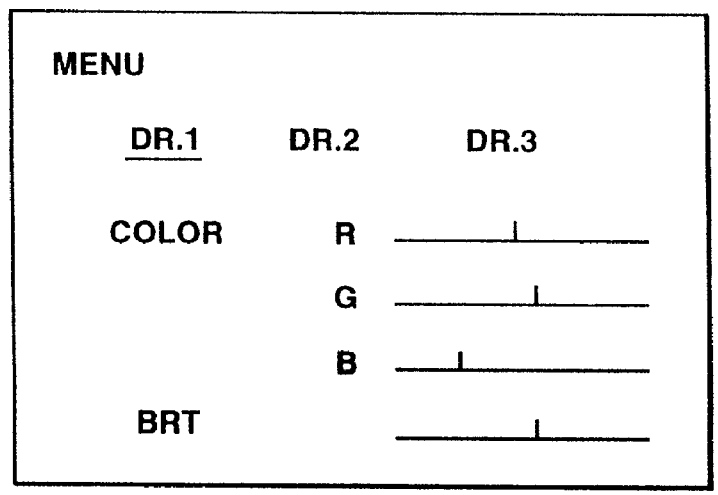
FIG. 46 is an explanatory diagram showing a setting modification screen associated with a doctor in the conventional system.

In the conventional system, a setting menu screen shown in FIG. 46 is displayed on the monitor or the like. Settings of tone and brightness are modified for each doctor. Handling for setting modification is therefore rather a nuisance. Moreover, an amount of data representing adjustment values which can be stored is limited because of the storage capacity of a memory. This leads to drawback that many setting items cannot be stored. In contrast, according to this embodiment, a setting for an operation concerning a desired item can be readily modified merely by inserting a memory card. Thus, the item can be set to an optimal value. Settings desired by a doctor can be attained by performing simple handling. Thus, a state suitable for a user can be established by performing simple handling, and endoscopic observation can be achieved under an optimal operational environment at all times.

According to the foregoing embodiment, simple handling or insertion of an associated memory card should merely be carried out according to a use situation, i.e., an object field relevant to an endoscopic examination or a doctor in charge thereof Thus, proper adjustment values can be set in various adjusting means for carrying out light adjustment control, tone adjustment, and contour enhancement. A proper operational environment can be established readily.

Incidentally, the endoscopic imaging system of this embodiment is not limited to an endoscope system for surgery in which a camera head is mounted on a rigid endoscope as described in conjunction with the previous embodiments. The endoscopic imaging system can also be adapted to an endoscope system for internal medicine in which a camera head is mounted on a soft endoscope or to an electronic endoscope having an imaging device incorporated therein.

Moreover, the memory card is not limited to a PC card having a memory incorporated therein. A card to which a compact memory card such as a smart medium can be detachably attached, or a card having a compact hard disk incorporated therein can also be adapted to the aforesaid embodiments.

Moreover, the card slot to which the memory card is connected is not limited to a structure formed in a lateral side of a CCU. Alternatively, a structure separated from the CCU and detachably attached to the CCU may be adopted.

Eighth Embodiment:

As shown in FIG. 32, an endoscopic imaging system 301 of this embodiment comprises a camera head 302 having an imaging means incorporated therein, a scope 303 connected to the camera head 302, a light source apparatus 304 for supplying illumination light to the scope 303, a camera control unit (hereinafter a CCU) 305 for processing a signal sent from the imaging means in the camera head 302, and a TV monitor 306 for displaying a standard video signal processed by the CCU 305. The scope 303 is a rigid endoscope such as a laparoscope used for, for example, a surgical procedure in the field of surgery.

When the endoscope imaging system 301 is put to use, a light guide 308 of the scope 303 is, as shown in FIG. 32, linked to the light source apparatus 304. Illumination light emanating from a lamp in the light source apparatus 304 passes through a diaphragm that is not shown, is converged by a lens, and falls on an opposing end surface of the light guide 308. The illumination light is transmitted to the scope 303 over the light guide 308, propagated through the scope, and emitted forward through the distal end of the scope 303. An object such as a patient's body cavity is then illuminated. An image represented by light reflected from the illuminated object is formed by the scope 303. The object image is projected by the imaging means in the camera head 302 through the scope 303.

A CCD 307 serving as the imaging means is located on the focal plane of an imaging lens in the camera head 302. The object image is formed on the image plane of the CCD 307 and converted photoelectrically. The CCD 307 is connected to the CCU 305 via a camera cable 309 in which a CCD driving signal transmission line and a CCD output signal transmission line are inserted. An output signal of the CCD 307 is sent to CCU 305 and subjected to various kinds of signal processing. A video signal output from the CCU 305 is sent to the TV monitor 306. A view image of the object is then displayed on the TV monitor 306.

The CCU 305 is provided with a CCD driver 310. The CCD driver 310 supplies a CCD driving signal to the CCD 307 over the CCD driving signal transmission line in the camera cable 309. A signal charge accumulated in the CCD 307 is then read. Moreover, the CCU 305 is provided with a preamplifier 311 and a pre-processing circuit 312. A CCD output signal read by the CCD 307 is transmitted to the CCU 305 over the CCD output signal transmission line in the camera cable 309. After the CCD output signal is amplified by the preamplifier 311 in the CCU 305 in order to compensate for a loss occurring during cable transmission, it is input to the pre-processing circuit 312.

On a succeeding side of the pre-processing circuit 312, there are an A/D converter 313 and a Y/C separation circuit 314. A CCD output signal input to the pre-processing circuit 312 is pre-processed by performing correlation double sample (CDS) and sample-and-hold (S/H). The resultant signal is then input to the A/D converter 313 and converted into a digital signal. The digital signal is then input to the Y/C separation circuit 314.

On a succeeding side of the Y/C separation circuit 314, there are an RGB matrix circuit 315 and a white balance/black balance adjustment circuit 316. A digital signal input to the Y/C separation circuit 314 is recomposed in conformity with the line sequential system. Digital signal Y, CR, and CB to be propagated through three channels are separated from one another, and input to the RGB matrix circuit 315. The digital signals are then converted into an RGB digital signal. Thereafter, the white balance/black balance adjustment circuit 316 adjusts the white balance and black balance of the signal.

On a succeeding side of the white balance/black balance adjustment circuit 316, there are a digital video processing circuit 317, a D/A converter 318, and a post-processing circuit 319. An RGB digital signal whose balance has been adjusted is digitally processed through enhancement, gamma correction, and character convolution performed by the digital video processing circuit 317. Thereafter, the signal is converted into an analog signal by the D/A converter 318, and then input to the post-processing circuit 319. The analog signal that is input to the post-processing circuit 319 is converted into a standard video signal and output to the TV monitor 306.

On the succeeding side of the digital video processing circuit 317, there are a memory 320, a JPEG compression circuit 321, and a PC card driver 322. A PC card slot 323 is connected to the PC card driver 322. A digital signal having undergone various kinds of signal processing is stored in the memory 320. A PC card 324 having a memory incorporated therein is mounted in the PC card slot 323. After a digital image signal read from the memory 320 is compressed by the JPEG compression circuit 321, it is recorded on the PC card 324 via a PC card driver 322.

Furthermore, the CPU 325 responsible for various kinds of control including control of recording an image on the PC card 324, a connection sensing means 326 for sensing the connected state of the PC card 324, and a character generator 327 for outputting medium information that includes the recorded quantity of image data on the PC card 324 and appears as a display on monitor 306 screen are included in the CCU 305. A release switch 329 used to give a handling instruction (release instruction) for image recording is formed on the front panel 328 of the CCU 305.

Figure 33:
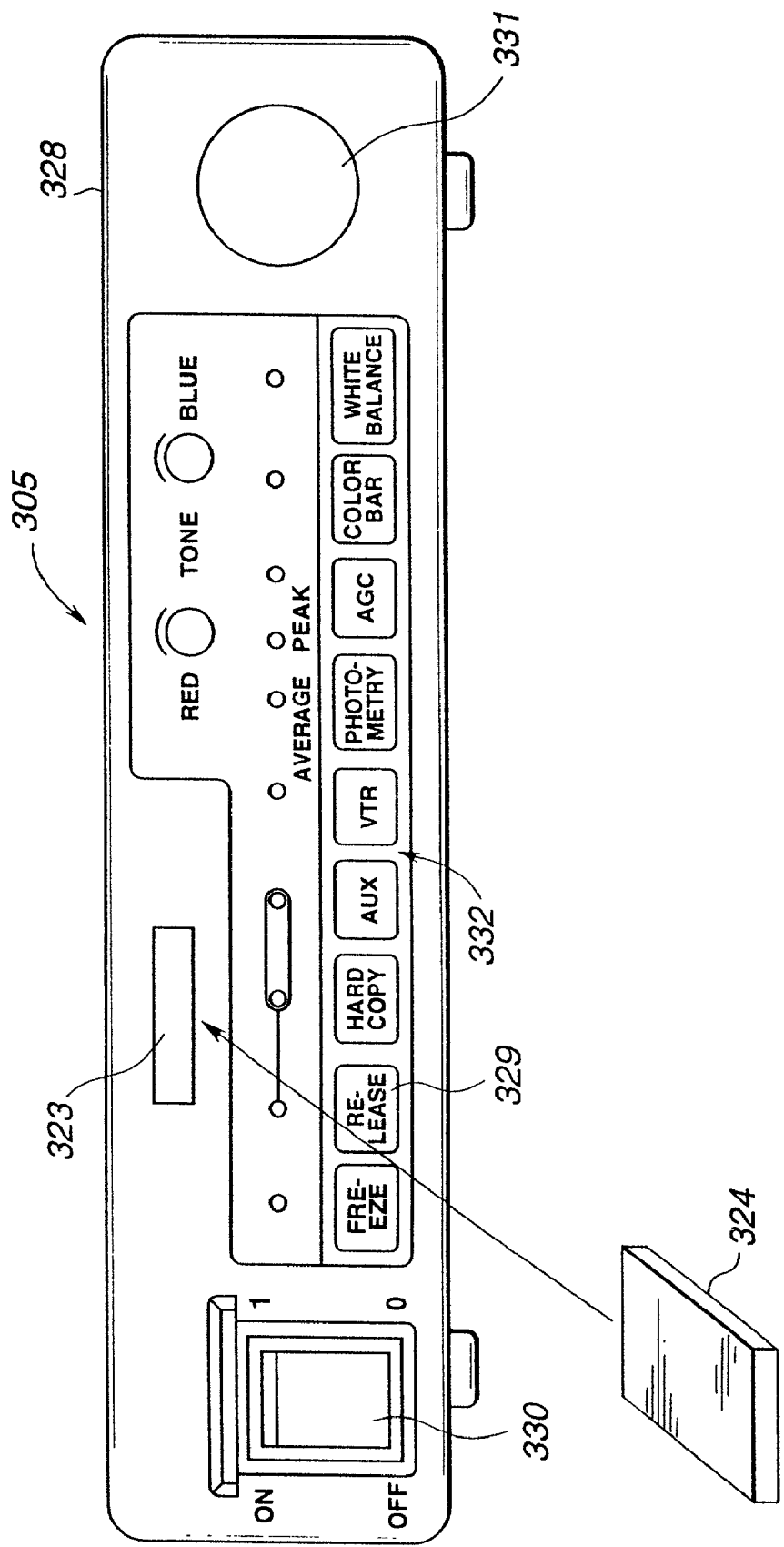

As shown in FIG. 33, a power switch 330, a connector receptor 331 to which the camera head 302 is plugged, the PC card slot 323, and operation switches 332 including the release switch 329 are arranged on the front panel 328 of the CCU 305.

Figure 34:
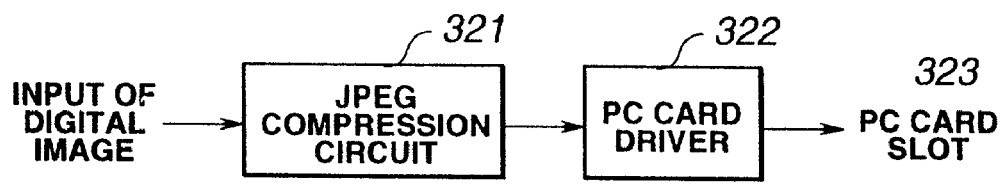
Figure 35:
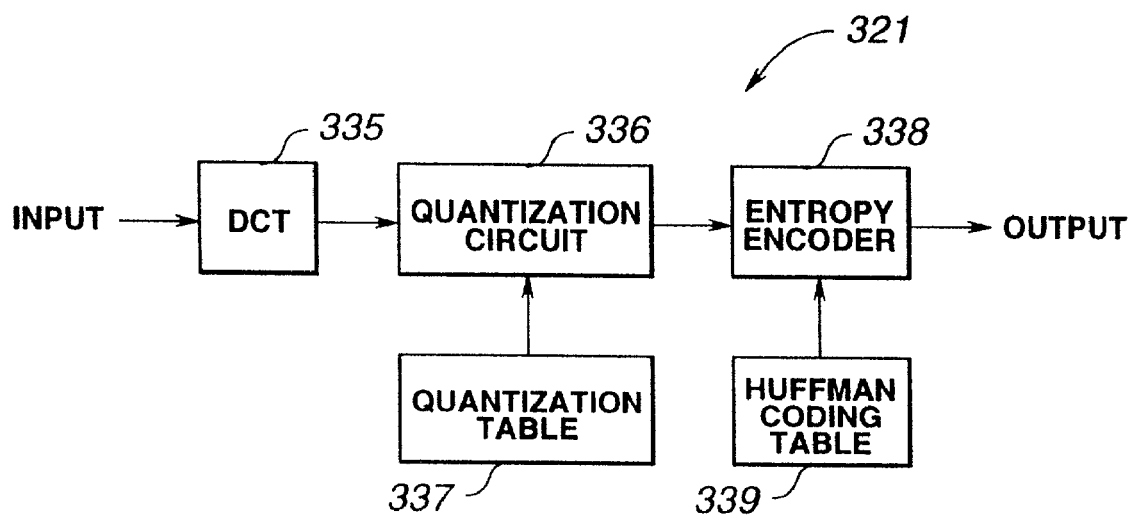

Referring to FIGS. 32, 34 and 35, the configuration and operation of an image recording unit for compressing and recording data of a projected image will be described. An image signal visualized and processed by the camera head 302 via the scope 303 is output to the TV monitor 306, displayed as an image on the TV monitor and then stored in the memory 320.

When the release switch 329 is pressed in order to record an endoscopic image, the CPU 325 sends a release signal to the memory 320. Image data representing a still image is read from the memory 320. The read image data is compressed by the JPEG compression circuit 321. The resultant data is sent to and recorded on the PC card 324 mounted in the PC card slot 323 via the PC card driver 322.

The JPEG compression circuit 321 is designed to carry out unilateral encoding based on the discrete cosine transform (DCT). The JPEG compression circuit 321 consists of a DCT circuit 335, a quantization circuit 336, a quantization table 337, an entropy encoder 338 and a Huffman coding table 339. Compression of image data is carried out as described below.

Assume that the precision or resolution of input image data is eight bits. The input image data is divided into blocks each composed of 8 by 8 pixels. The DCT circuit 335 performs two-dimensional DCT on a block composed of 8 by 8 pixels. Thereafter, the quantization circuit 336 linearly quantizes a DCT coefficient using the quantization table 337 that lists a set of discrete values in steps whose size is different from coefficient to coefficient. By modifying the values listed in the quantization table 337, image quality and a magnitude of encoding can be controlled. The entropy encoder 338 uses the Huffman coding table 339 to encode image data as entropy. Specifically, a DC component and AC components of a quantized DCT coefficient are encoded independently. Resultant code data is output as image data. Herein, the Huffman coding is adopted as the entropy encoding.

During image recording, the CPU 325 reads information of a storage capacity for image data on the PC card 324 and information of the connected state of the PC card 324 sensed by the connection sensing means 326. Information of the image data recorded on the medium is output. The connected state of the PC card 324 is sensed by checking a high-level or low-level signal that is output from the connection sensing means 326 according to whether or not the PC card 324 is inserted in the PC card slot 323.

The CPU 325 includes a remaining capacity sensing means for sensing a remaining storage capacity on the PC card 324, and an arithmetic calculation means for calculating the number of recordable images according to the sensed remaining storage capacity. Medium information including the number of recordable images, which is output from the CPU 325, is output as character information from the character generator 327. The character information is superimposed on an image in a screen on the TV monitor 306.

Figure 36:
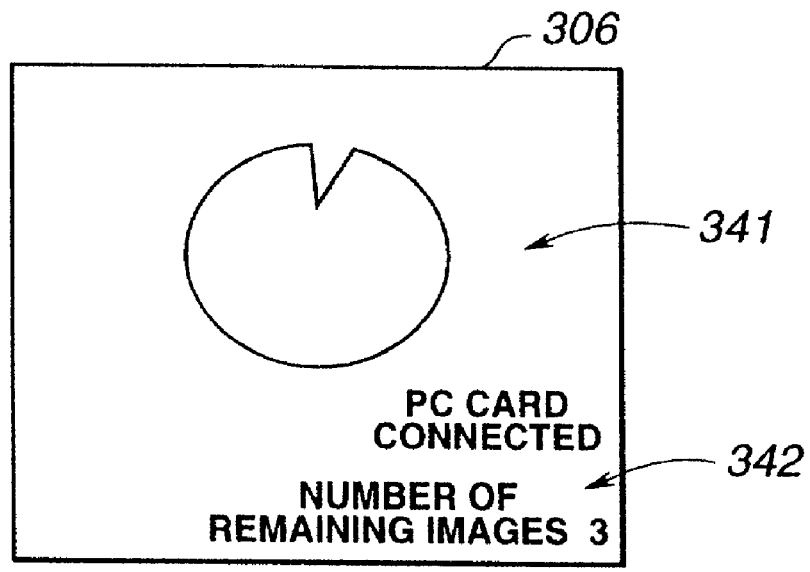

FIG. 36 shows an example of a display screen on the TV monitor 306. Medium information 342 concerning the connected state of the PC card 324 and the recorded state of image data on the PC card 324 is displayed together with an endoscopic image 341 projected by the camera head 302 at, for example, a right lower corner of the screen on the TV monitor 306. "PC card connected" indicating that the PC card 324 has been connected normally, and "The number of remaining images is 3" indicating the number of images recordable on the PC card 324 are displayed.

When an endoscopic image is thus recorded using a PC card, a still image having little deterioration can be recorded and stored at low cost. Moreover, when the image is recorded, medium information such as the recording capacity of image data on the PC card can be superimposed on a view image on a monitor. A user can therefore recognize the connected state of the PC card and the number of remaining recordable images readily.

When digital image data is compressed and recorded on a medium such as a PC card, the number of remaining recordable images varies depending on a level of compressibility of data or a storage capacity on a medium. It is therefore hard for a user to grasp the recording capacity of image data. According to this embodiment, medium information can be checked accurately. It can be prevented that recording a necessary image fails because of imperfect connection of the PC card or an insufficient storage capacity.

Ninth Embodiment:

The ninth embodiment is an example of a configuration where medium information is displayed on a liquid crystal display (hereinafter an LCD) on the front panel of a CCU.

Figure 37:
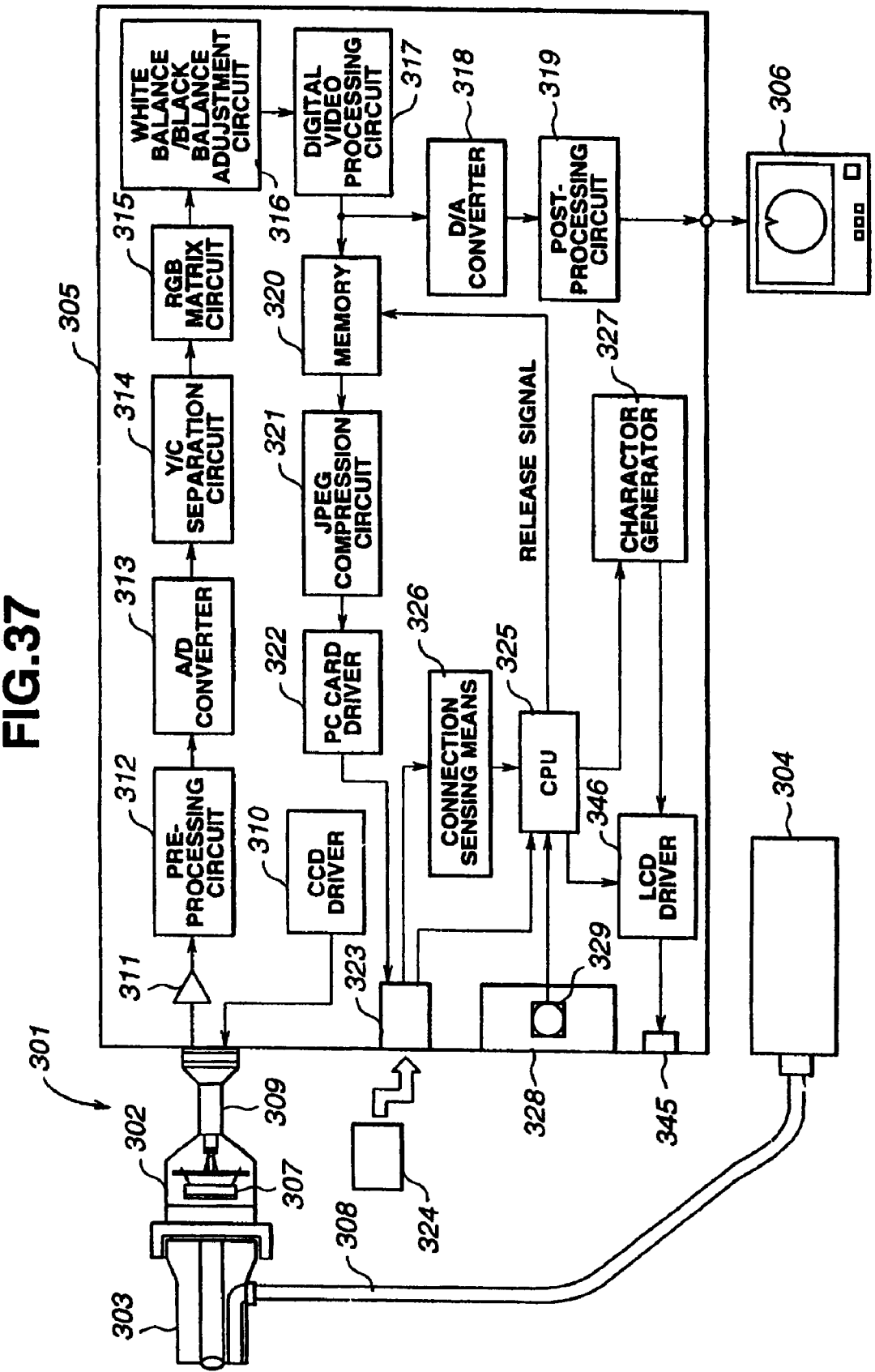

As shown in FIG. 37, the CCU 305 has, in addition to the components of the eighth embodiment shown in FIG. 32, and LCD 345 formed on the front panel thereof. The CCU 305 also has an LCD driver 346 for driving the LCD 345 therein. The LCD driver 346 is connected to the CPU 325 and character generator 327. Character information of medium information generated by the character generator 327 is displayed on the LCD 345.

The components of this embodiment other than the components relevant to display of medium information and the operation thereof are identical to those of the eighth embodiment. The description of those components will thus be omitted.

During image recording, the CPU 325 reads information of a storage capacity for image data on the PC card 324 and information of the connected state of the PC card sensed by the connection sensing means 326 in the same manner as that of the eighth embodiment. The number of recordable images or the like is then calculated. The information of the image data recording capacity on the medium is then output. Medium information such as the number of recordable images output from the character generator 327 is output as character information from the character generator 327 to the LCD driver 346. The medium information is displayed on the LCD 345 on the front panel of the CCU 305.

Figure 38:
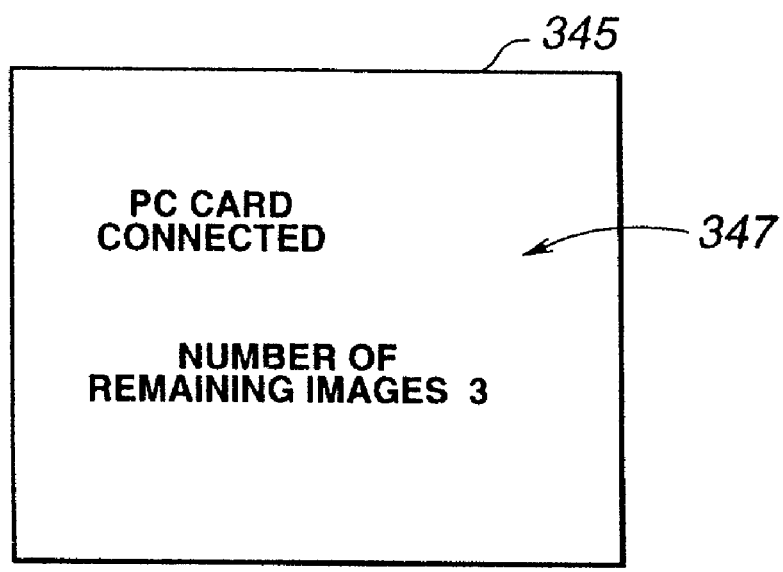
FIGS. 37 and 38 relate to a ninth embodiment of the present invention.

FIG. 38 shows an example of an information display on the LCD 345. Medium information identical to the one in the eighth embodiment, that is, medium information 347 concerning the connected state of the PC card and the recorded state of image data on the PC card 324 is displayed on the LCD 345. "PC card connected" indicating that the PC card 324 has been connected normally, and "The number of remaining images is 3" indicating that the number of remaining images recordable on the PC card 324 are displayed.

Medium information such as the recording capacity of image data on a PC card is displayed on the front panel of a CCU or the like separately from a view image on a monitor. A user can therefore recognize the connected state of the PC card and the number of remaining recordable images as readily as he/she can in the eighth embodiment. Moreover, according to the ninth embodiment, an endoscopic image alone is displayed on the monitor. The display of medium information will not hinder viewing of an endoscopic image. The user can recognize the state of a medium any time without hampering observation or surgery.

Tenth Embodiment:

The tenth embodiment is an example of a configuration including an alarm means for displaying medium information only when it is needed and for giving an alarm to a user.

Figure 39:
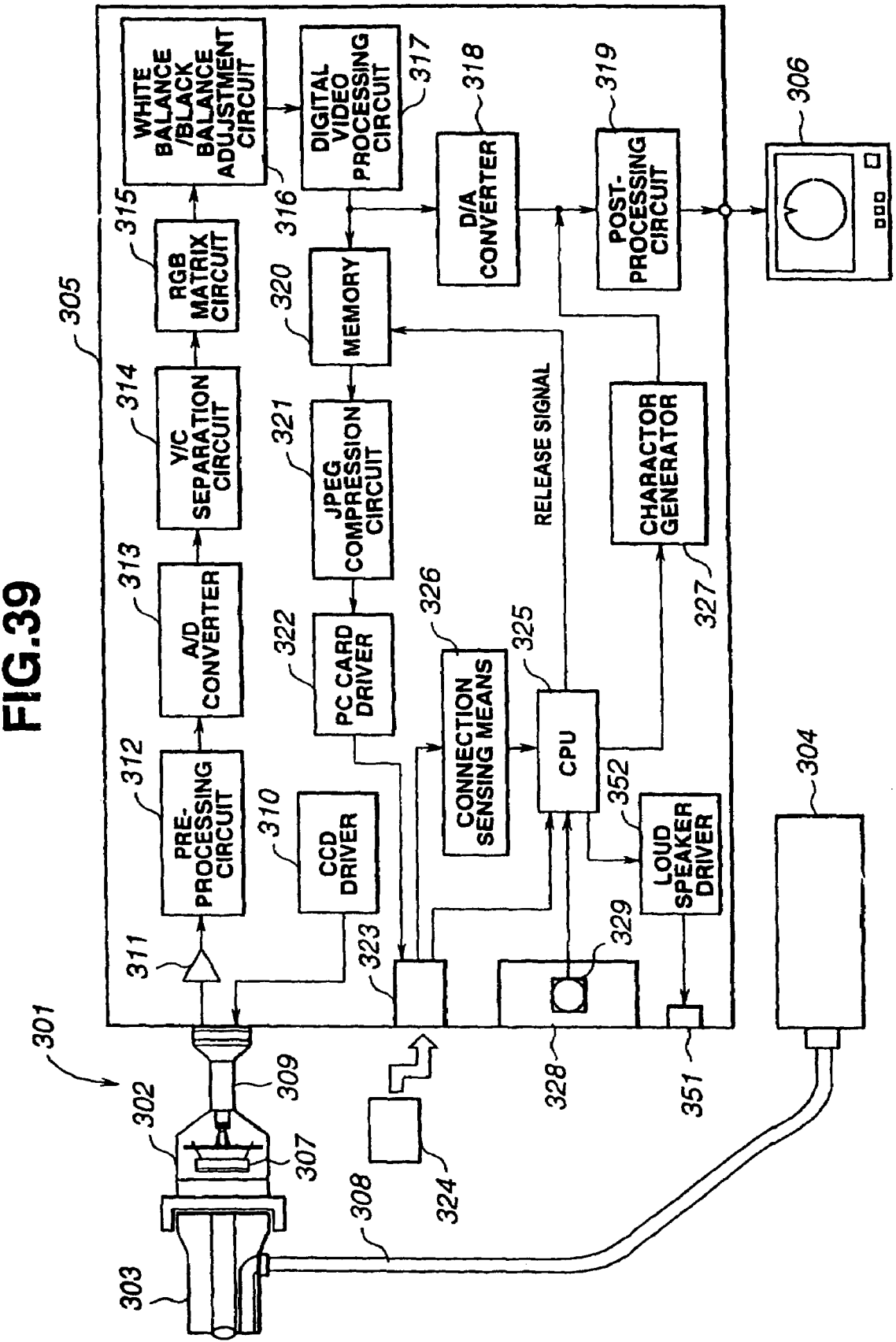
FIGS. 39 and 40 relate to a tenth embodiment of the present invention.

The CCU 305 has, in addition to the components of the eighth embodiment shown in FIG. 32, as shown in FIG. 39, a loudspeaker 351 for alarming. The loudspeaker 351 is connected to a loudspeaker driver 352 for converting a notification signal output from the CPU 325 into a voice signal. The components of the tenth embodiment other than the components relevant to the alarming means are identical to those of the eighth embodiment. The description of those components will thus be omitted.

According to the tenth embodiment, when needed, or specifically, when the PC card 324 is not mounted normally or the number of remaining images recordable on the PC card 324 becomes zero, medium information is also displayed or superimposed on an image in a screen on the TV monitor 306. Thus, a user's attention is called.

The CPU 325 calculates the number of recordable images using information of a storage capacity for image data on the PC card 324, and information of the connected state of the PC card 324 sensed by the connection sensing means 326. When it is necessary to inform a user of medium information, for example, when image recording cannot be achieved normally, the medium information is output to the character generator 327. At the same time, a notification signal is output to the loudspeaker driver 352. The medium information sent from the CPU 325 is output as character information from the character generator 327 and superimposed on an image in a screen on the TV monitor 306. In addition, an audio message saying, for example, "Replace the PC card with a new one," is uttered by the loudspeaker 351.

Figure 40:
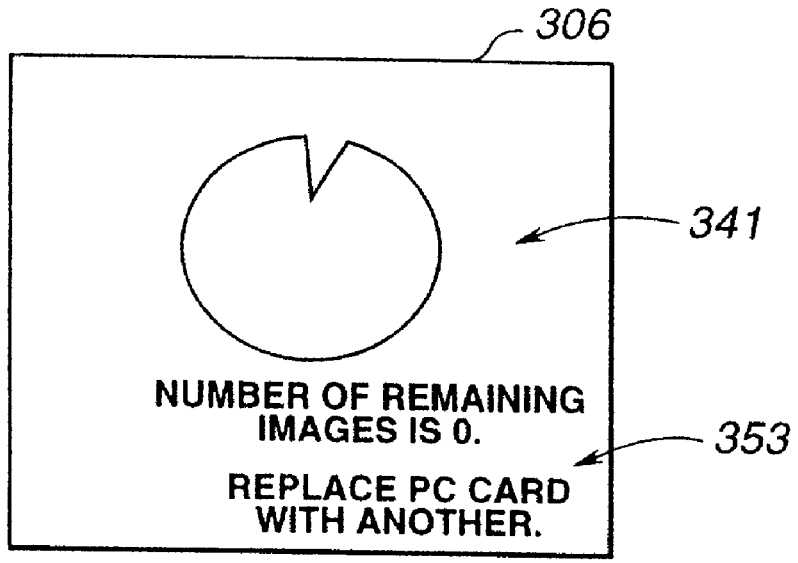

FIG. 40 shows an example of a display screen on the TV monitor 306. Medium information 353 concerning the connected state of the PC card 324 and the recorded state of image data on the PC card 324 is displayed together with an endoscopic image 341, which is projected by the camera head 302, at, for example, the right lower corner of a screen on the TV monitor 306 only when it is needed. In this example, when the number of images recordable on the PC card 324 becomes zero, a message saying "The number of remaining images is zero. Replace the PC card with another." is displayed in order to prompt a user to replace a medium with another.

As mentioned above, only when medium information such as the recorded image data on the PC card is needed, it is superimposed on view image on the monitor or a voice is uttered. A user can therefore recognize the connected state of the PC card or the recorded state of image data readily at an appropriate time without discontinuing observation or hampering surgery. Thus, a failure in recording an image, the loss of a necessary image due to overwriting of a recorded image, or any other mistake can be prevented from being made during image recording.

According to a variant concerning notification of medium information, before the number of recordable images becomes zero, when the number of recordable images becomes equal to or smaller than a given value (for example, 2), a display may be provided in order to inform a user of the fact.

Eleventh Embodiment:

The eleventh embodiment is an example of a configuration including a reproducing means for reproducing image data of a still image recorded on a PC card.

Figure 41:
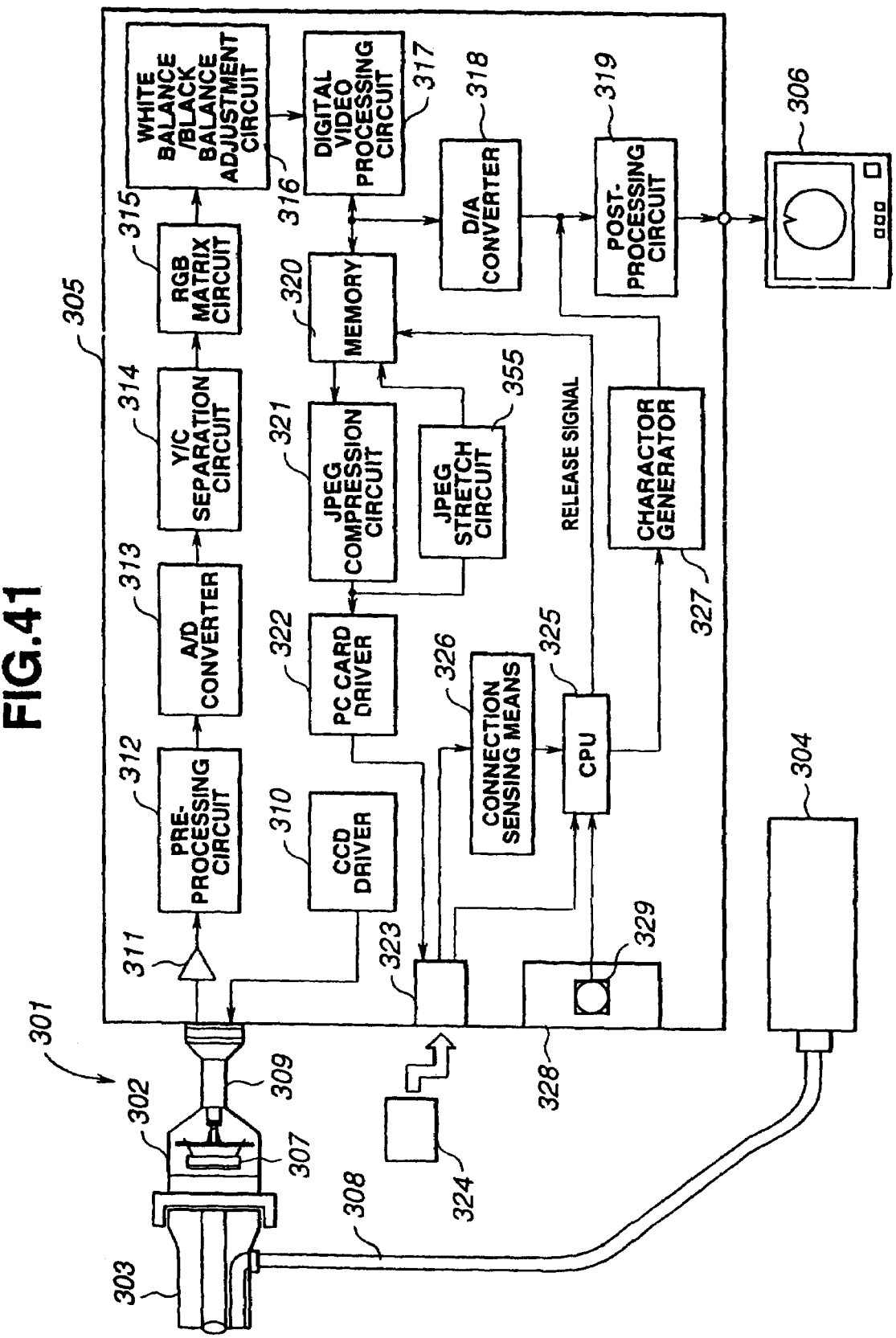
Figure 43:
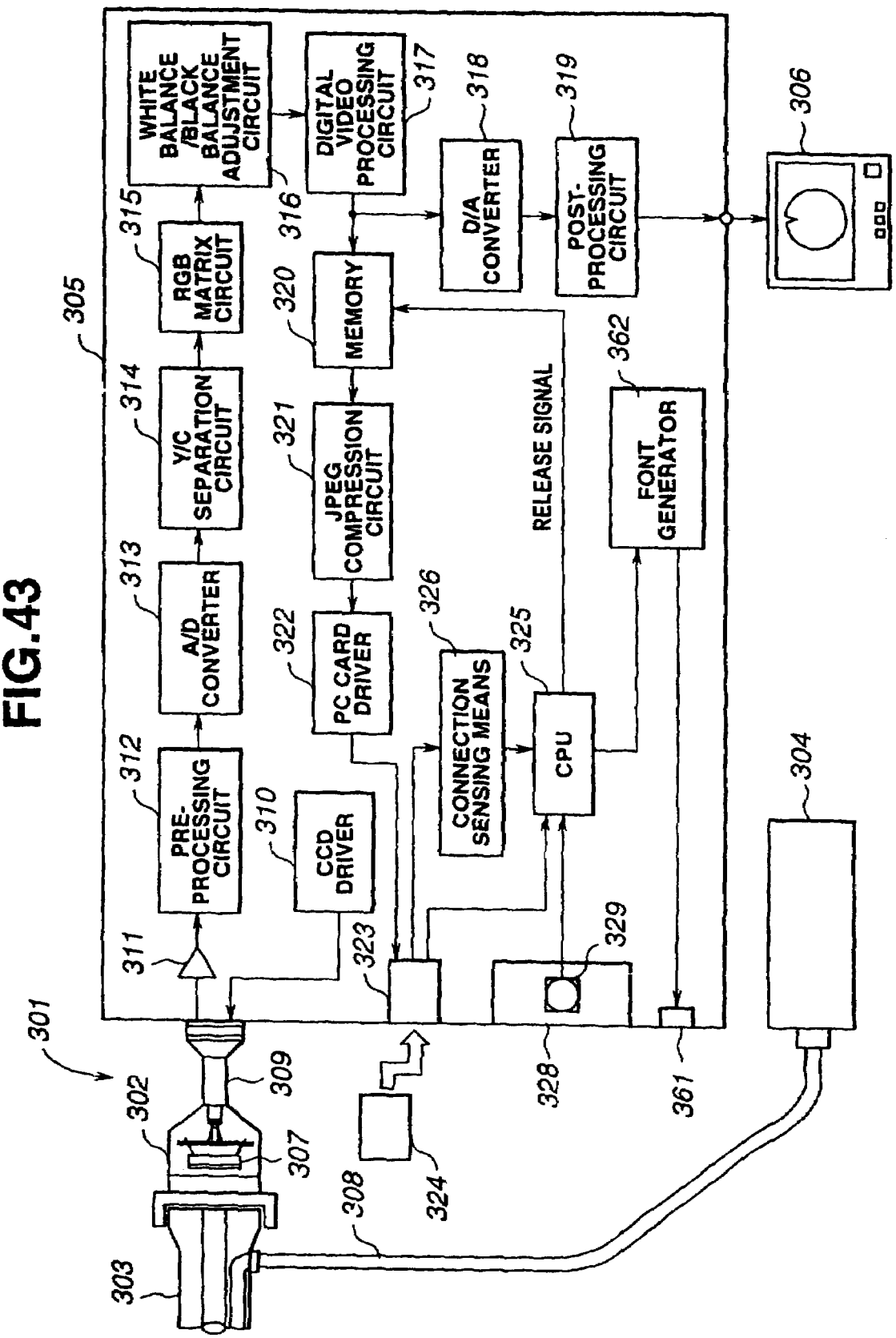
FIGS. 43 and 44 relate to a twelfth embodiment of the present invention.
Figure 44:
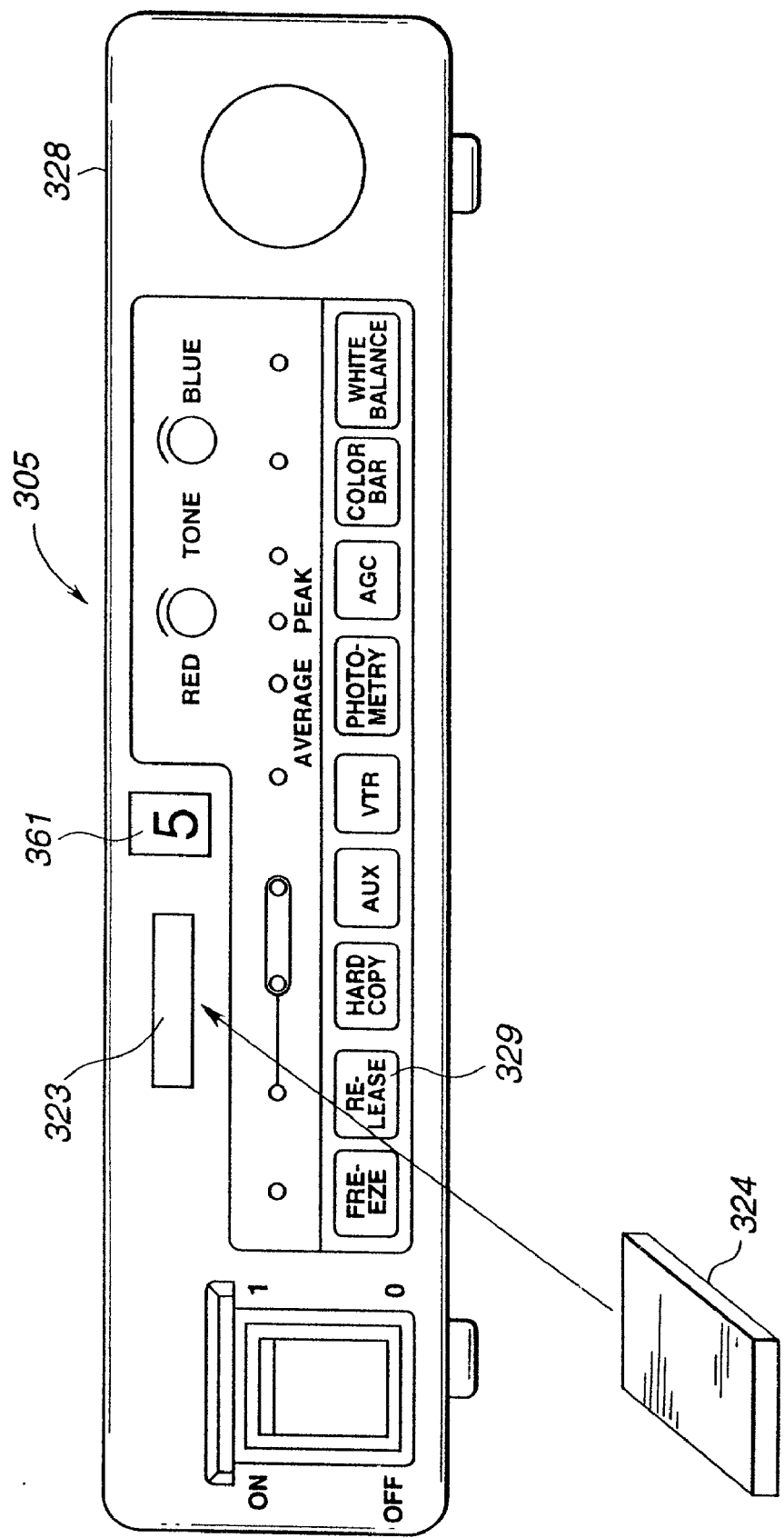

The CCU 305 has, in addition to the components of the eighth embodiment shown in FIG. 41, a JPEG stretch circuit 355 connected in parallel to the JPEG compression circuit 321 between the PC card driver 322 and memory 320. The JPEG stretch circuit 355 processes data by reversing the procedure followed by the JPEG compression circuit 321. In other words, the JPEG stretch circuit 355 stretches image data that has been encoded to be compressed, and thus restores it to original image data. The components other than the components relevant to the reproducing means are identical to those of the eighth embodiment. The description of those components will therefore be omitted.

For reproducing image data of a still image recorded on the PC card 324, image data is read from the PC card 324 via the PC card driver 322 in response to an instruction sent from the CPU 325. The image data is stretched by the JPEG stretch circuit 355, and then stored in the memory 320. The stretched image data is read from the memory 320, and converted into a standard video signal by the D/A converter 318 and post-processing circuit 319. The resultant image data is output to and displayed on the TV monitor 306.

Figure 42:
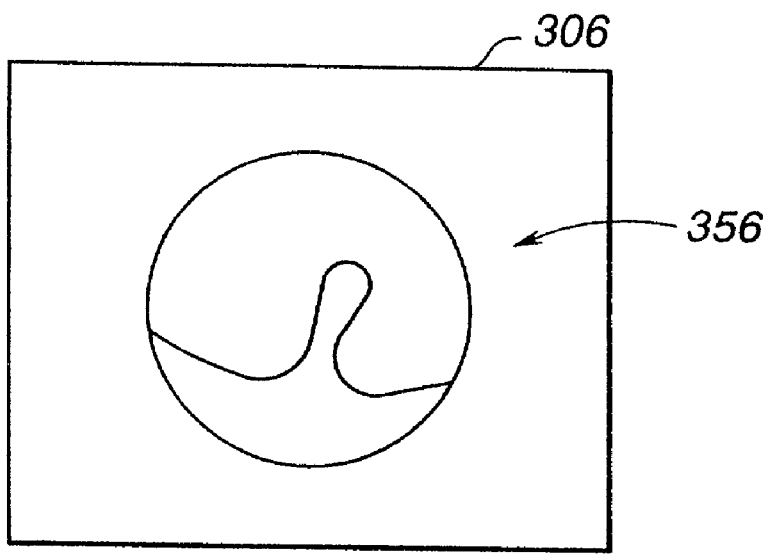
FIGS. 41 and 42 relate to an eleventh embodiment of the present invention.

FIG. 42 shows an example of a display screen on the TV monitor 306. A still image 356 recorded on the PC card 324 is reproduced and displayed in a screen on the TV monitor 306.

Since a still image recorded on a PC card can thus be displayed, a user can check if the recorded image is necessary. Consequently, unnecessary images can be identified and deleted. A larger number of necessary images can be recorded on the PC card. Moreover, a PC card must be replaced with another at a reduced frequency during an endoscopic examination. The labor of replacing a medium with another can be minimized, and the cost required for the running of a medium can be reduced.

Twelfth Embodiment:

The twelfth embodiment is an example of a configuration including an LED for displaying a releasing count on the front panel of a CCU.

CCU 305 has, in addition to the components of the eighth embodiment shown in FIG. 32, as shown in 43, an LED 361 for displaying numerals, such as a seven-segment display formed on the front panel thereof. Moreover, a font generator 362 for driving the LED 361 for display is incorporated in the CCU 305. The font generator 362 is connected to the CPU 325. Based on information concerning release performed during image recording which is output from the CPU 325, information of a releasing count is indicated with numerals on the LED 361. The components of the twelfth embodiment other than the components relevant to display of the releasing count are identical to those of the eighth embodiment. The description of those components will thus be omitted.

When the release switch 329 is pressed in order to record an endoscopic image, the CPU 325 sends a release signal to the memory 320. Image data of a still image is then read from the memory 320. The read image data is compressed by the JPEG compression circuit 321, and sent to and recorded on the PC card 324 mounted on the PC card slot 323 via the PC card driver 322. At this time, the CPU 325 sends release information to the font generator 362, and numerals indicating a releasing count are displayed on the LED 361. The releasing count is incremented by one with every release.

As mentioned above, a display means for displaying medium information concerning the number of images that are represented by image data and recordable on the PC card is formed on the front panel of a CCU or the like. A user can therefore readily recognize recording data such as the number of remaining images recordable on the PC card.

The adaptation of the endoscopic imaging system of this embodiment is not limited to an endoscope system for surgery in which a camera head is mounted on a rigid endoscope as described in conjunction with the previous embodiments. The endoscopic imaging system can also be adapted to an endoscope system for internal medicine in which a camera head is mounted on a soft endoscope or an electronic endoscope having an imaging device incorporated therein.

Moreover, the PC card is not limited to a card having a memory incorporated therein. Even a card to which a compact memory card such as a smart medium can be detachably attached or a card having a compact hard disk incorporated therein can be adapted to the aforesaid embodiments.

Moreover, the PC card slot to which a PC card is connected is not limited to a structure formed on the front panel of a CCU. Alternatively, a structure provided separately from the CCU and detachably attached thereto may be used in connection with the present invention.

According to the present invention, it is apparent that a wide range of different embodiments can be constructed without a departure from the spirit and scope of the present invention. This invention is limited by the appended claims but not restricted to any specific embodiments described herein.

What is claimed is:

1. An endoscopic imaging system, comprising:
   a signal processor for processing a video signal sent from an imaging device;
   a plurality of adjusting elements for adjusting various properties of a video signal sent from said signal processor;
   an electrical connector for enabling detachable connection at an external storage unit to said endoscopic imaging system for storing adjustment values to be set by said adjusting elements; and
   a controller for modifying settings of said adjusting elements according to said adjustment values stored in said external storage unit.

2. An endoscopic imaging system according to claim 1, wherein said adjusting elements include at least one of a white balance adjusting element, a light adjusting element, a tone adjusting element, and a contour enhancing element.

3. An endoscopic imaging system according to claim 1, wherein said adjustment values include a changeable value.

4. An endoscopic imaging system according to claim 1, wherein said adjustment values are stored as a plurality of types of adjustment values on separate external storage units.

5. An endoscopic imaging system according to claim 1, wherein said adjustment values are specified as a set of adjustment values for each of a plurality of fields in which said endoscopic imaging system is used, and wherein each set of adjustment values are stored on separate external storage units.

6. An endoscopic imaging system according to claim 3, wherein said adjustment values are specified as a set of adjustment values for each of a plurality of operators handling said endoscopic imaging system, and wherein each set of adjustment values are stored on separate external storage units.

7. An endoscopic imaging system according to claim 5, further comprising an alarm circuit for giving an alarm when an external storage unit other than an external storage unit, on which adjustment values associated with an intended field or operator are stored is connected to said signal processing apparatus.

8. An endoscopic imaging system according to claim 6, further comprising an alarm circuit for giving an alarm when an external storage unit other than an external storage unit on which adjustment values associated with an intended field or operator are stored is connected to said signal processing apparatus.

9. An endoscopic imaging system comprising:
   an imaging means for projecting an object image; and
   a signal processing means for processing an image signal outputted from said imaging signal means, wherein said signal processing means comprises:
   a signal processing circuit for processing said image signal outputted from said imaging means to produce a video signal;
   a plurality of adjusting circuits for adjusting the properties of the video signal based on an adjustment value;
   a portable recording medium slot to which a portable recording medium for storing adjustment value is detachably connectable; and
   a control circuit for controlling operations of said adjusting circuits according to the adjustment value stored in a portable recording medium connected to said portable recording medium slot.

10. An endoscopic imaging system according to claim 9, wherein said adjustment values include a changeable value.

* * * * *